United States Patent
Hirakawa et al.

(10) Patent No.: US 11,694,789 B2
(45) Date of Patent: Jul. 4, 2023

(54) MEDICAL EXAMINATION SUPPORT APPARATUS

(71) Applicant: FUJIFILM Corporation, Tokyo (JP)

(72) Inventors: Tsuyoshi Hirakawa, Tokyo (JP); Hiroshi Hiramatsu, Tokyo (JP); Haruyasu Nakatsugawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 274 days.

(21) Appl. No.: 16/443,069

(22) Filed: Jun. 17, 2019

(65) Prior Publication Data

US 2020/0005934 A1 Jan. 2, 2020

(30) Foreign Application Priority Data

Jun. 29, 2018 (JP) .............................. JP2018-125089

(51) Int. Cl.
*G16H 80/00* (2018.01)
*G16H 40/20* (2018.01)
(Continued)

(52) U.S. Cl.
CPC ..... *G16H 40/20* (2018.01); *G06Q 10/063114* (2013.01)

(58) Field of Classification Search
CPC ........ G16H 10/60; G16H 40/67; G16H 80/00; G16H 15/00; G16H 40/20; G16H 50/20;
(Continued)

(56) References Cited

U.S. PATENT DOCUMENTS

2005/0265101 A1 12/2005 Nambu et al.
2007/0276809 A1 11/2007 Yoshida
(Continued)

FOREIGN PATENT DOCUMENTS

CN 106775753 A 5/2017
JP 2007-188239 A 7/2007
(Continued)

OTHER PUBLICATIONS

Fujifilm Medical appeals advanced medical IT solutions such as "Synapse VNA" and "CITA Clinical Finder"; Jul. 14, 2017; Internet URL: https://www. Innervision.co.jp/report/imhs/2017/repo/fujifilm [Seach on May 17, 2021]; previously submitted within three months from an Office Action from the Japanese Patent Office and currently resubmitted along with English language translation.
(Continued)

*Primary Examiner* — Maroun P Kanaan
(74) *Attorney, Agent, or Firm* — Studebaker & Brackett PC

(57) ABSTRACT

A medical examination support apparatus includes: a display screen generation unit that generates a display screen for displaying a medical examination process and identification information of a patient so as to be associated with each other for each of a plurality of patients; and an unread management unit that displays a status, which includes information indicating that the medical examination process has been unread, or information indicating that the medical examination process has been read, or both the pieces of information, on the display screen. In a case where there is a revision in the medical examination process whose status is unread or read, the unread management unit displays the status of the medical examination process, which has been revised, in a display mode different from display modes indicating unread and read.

20 Claims, 14 Drawing Sheets

(51) Int. Cl.
*G06Q 10/06* (2023.01)
*G06Q 10/0631* (2023.01)

(58) Field of Classification Search
CPC ........ G16H 10/65; G16H 40/63; G16H 50/30; G06Q 10/063114
See application file for complete search history.

(56) References Cited

U.S. PATENT DOCUMENTS

| | | | |
|---|---|---|---|
| 2012/0136221 A1* | 5/2012 | Killen | G16H 40/67 600/300 |
| 2013/0014063 A1 | 1/2013 | Bocking | |
| 2015/0025904 A1* | 1/2015 | Rao | G16H 80/00 705/2 |
| 2016/0203286 A1 | 7/2016 | Okabe et al. | |
| 2016/0224737 A1 | 8/2016 | Okabe et al. | |
| 2017/0331777 A1* | 11/2017 | Brisebois | H04L 51/212 |
| 2018/0137943 A1* | 5/2018 | Webb, III | H04L 67/06 |

FOREIGN PATENT DOCUMENTS

| | | |
|---|---|---|
| JP | 2007-316872 A | 12/2007 |
| JP | 2013-149267 A | 8/2013 |
| JP | 2016-130983 A | 7/2016 |
| JP | 2016-143205 A | 8/2016 |
| JP | 2016-192157 A | 11/2016 |
| JP | 2017-129922 A | 7/2017 |
| JP | 2018-092419 A | 6/2018 |
| WO | 2003/083674 A1 | 10/2003 |

OTHER PUBLICATIONS

An Office Action; "Decision of Refusal," mailed by the Japanese Patent Office dated Sep. 28, 2021, which corresponds to Japanese Patent Application No. 2018-125089 and is related to U.S. Appl. No. 16/443,069; with English language translation. Cited references therein have been previously submitted.

Fujifilm Medical appeals advanced medical IT solutions such as "Synapse VNA" and "CITA Clinical Finder"; Jul. 14, 2017; Internet URL: https://www. Innervision.co.jp/report/imhs/2017/repo/fujifilm [Seach on May 17, 2021].

An Office Action; "Notice of Reasons for Refusal," mailed by the Japanese Patent Office dated May 25, 2021, which corresponds to Japanese Patent Application No. 2018-125089 and is related to U.S. Appl. No. 16/443,069 with English language translation.

An Office Action mailed by the Japanese Patent Office dated Jul. 26, 2022, which corresponds to Japanese Patent Application No. 2021-120928 and is related to U.S. Appl. No. 16/443,069.

* cited by examiner

| | C01 | C02 | C03 | C04 |
|---|---|---|---|---|
| L01 | PATIENT ▲ | UNREAD NUMBER MANAGEMENT | | RADIATION |
| L02 | YAGI TARO 00000001 03/22/1969 INFECTION ALLERGY AGE: 48 ♀ ▽M | UNREAD (ONESELF): 4 CASES<br>UNREAD (ONESELF'S DEPARTMENT): 1 CASE<br>UNREAD (OTHER DEPARTMENTS): 2 CASES | 8/22 14:06 HB: 10.4 g/dL ☐ L INR: 0.8<br>AST: 21.0 U/L  IRREGULARITY: NEGATIVE | 6/16 14:14 IMAGE MRI:<br>CT: REPORT ● |
| L03 | YAGI JIRO 04240171 06/29/1930 INFECTION ALLERGY AGE: 87 ♀ ▽M | UNREAD (ONESELF): 0 CASE<br>UNREAD (ONESELF'S DEPARTMENT): 0 CASE<br>UNREAD (OTHER DEPARTMENTS): 0 CASE | 8/22 14:06 HB: 12.1 g/dL INR: 1.2<br>AST: 13.0 U/L  IRREGULARITY: NEGATIVE | CT: MRI: |

82

|  |  | STATUS | | | |
|---|---|---|---|---|---|
|  |  | UNREAD | | READ | IMPORTANT |
|  |  | NEW | REVISED | | |
| REQUESTER | ONESELF | ● | ◪ | | ▲ |
| | ONESELF'S DEPARTMENT | ○ | ▱ | | △ |
| | OTHER DEPARTMENTS | ○ | ▱ | | △ |

FIG. 15

| TIMELINE | UNREAD: 0 CASE REVISED: 1 CASE | 01/01/2017 TO 01/01/2018 | | | | |
|---|---|---|---|---|---|---|
| EXAMINATION TYPE | NUMBER OF CASES | 06/11/18 | 06/12/18 | 06/13/18 | 06/14/18 | 06/14/18 | 06/14/18 |
| CT | 1 | | CT<br>IMAGE REPORT | | | |
| MRI | 0 | | | | | |
| ENDOSCOPE | 1 | | | | | |

201

| DATA TYPE | EXAMINATION TYPE | STATUS | PATIENT |
|---|---|---|---|
| REPORT | CT | REVISED | FUJI GORO |
| IMAGE | ENDOSCOPE | UNREAD | YAGI TARO |
| REPORT | MRI | UNREAD | FUJI ICHIKO |
| IMAGE | CT | UNREAD | FUJI JIRO |
| IMAGE | CT | UNREAD | YAGI JIRO |
| REPORT | ECHOCARDIOGRAPHY | UNREAD | YAGI ICHIRO |
| REPORT | CT | REVISED | YAGI SABURO |
| REPORT | PATHOLOGY | UNREAD | FUJI ICHIKO |

UNREAD DATA LIST

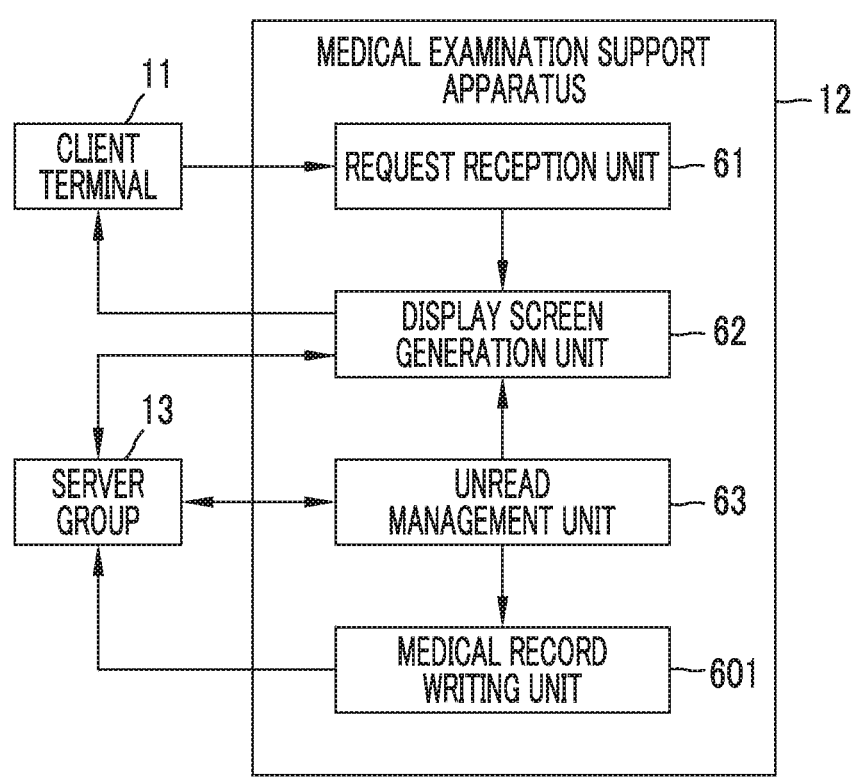

MEDICAL EXAMINATION SUPPORT APPARATUS

CROSS-REFERENCE TO RELATED APPLICATIONS

This application claims priority under 35 U.S.C § 119(a) to Japanese Patent Application No. 2018-125089 filed on Jun. 29, 2018. The above application is hereby expressly incorporated by reference, in its entirety, into the present application.

BACKGROUND OF THE INVENTION

1. Field of the Invention

The present invention relates to a medical examination support apparatus.

2. Description of the Related Art

In the medical field, in order for medical staff members, such as doctors and laboratory technicians, to smoothly advance medical practices, examinations, and the like, an integrated medical examination support apparatus allowing the processes and results of medical examinations and the like to be shared by medical staff members, medical departments, or the like has been used. The medical examination support apparatus supports medical examinations, for example, by displaying a list in which the processes and results of medical examinations are listed for a plurality of patients so that the list is provided to medical staff members (JP2016-143205A, corresponding to US2016/224737A1). In addition, there is a medical examination support apparatus that supports medical examinations, for example, by displaying a so-called timeline, in which the processes and results of medical examinations and the like of each patient are listed in time series for each patient, so that the medical examination processes and results of the patient are easily understood (JP2013-149267A).

In addition to the above, in fields other than the medical field, setting the degree of importance or urgency or the like for a group in a case where a document is shared and viewed by a plurality of persons and managing a case where one person in a group views a document as read is known (JP2007-188239A).

SUMMARY OF THE INVENTION

The medical examination support apparatus displays a list or a timeline screen regarding a patient, a medical examination process, and the like as described above. However, in the case of a list regarding a patient, a medical examination process, and the like, for example, in a case where the number of patients is large or the number of items including a medical examination is large, medical staff members may overlook a new image and a new report even though the new image and the new report are present. In the case of a timeline, in a case where a plurality of examinations and the like are performed at the same time or the number of examination items is large, medical staff members may overlook a new image, a new report, and the like. Since such oversight or delay of treatment due to oversight (temporary oversight) may eventually affect the medical condition of the patient, support for preventing the oversight as much as possible is required.

For this reason, the medical examination support apparatus disclosed in JP2016-143205A reduces oversights by attaching a mark indicating "unread" to an unread item, which is a new item and has not yet been viewed, in the list regarding a patient, a medical examination process, and the like. The medical examination support apparatus disclosed in JP2013-149267A reduces oversights by attaching an "unread" mark to an unread image or the like in the timeline.

On the other hand, the content may be revised after an image, a report, or the like is viewed. In the medical field, revisions of images, reports, and the like are, for example, addition or replacement of an image captured under the conditions different from those at the time of acquisition of the original image or addition or change of findings by doctors and the like, and affect the treatment plan. For this reason, compared with revisions for the purpose of correction of an error or addition of content in a general document and the like, revisions of images, reports, and the like in the medical field are particularly important. Therefore, it is also possible to manage the revised image, report, and the like as "unread" again. In the medical field, however, it is desirable to display the revised image, report, and the like so as to be distinguished from "unread".

Therefore, it is an object of the invention to provide a medical examination support apparatus for preventing oversights by alerting that there has been a revision in a medical examination process, such as an image or a report.

A medical examination support apparatus of the invention comprises: a display screen generation unit that generates a display screen for displaying a medical examination process and identification information of a patient so as to be associated with each other for each of a plurality of patients; and an unread management unit that displays a status, which includes information indicating that the medical examination process has been unread, or information indicating that the medical examination process has been read, or both the pieces of information, on the display screen. In a case where there is a revision in the medical examination process whose status is unread or read, the unread management unit displays the status of the medical examination process, which has been revised, in a display mode different from display modes indicating unread and read.

It is preferable that the unread management unit displays the status of the medical examination process, which is requested by a person who views the display screen, and the status of the medical examination process, which is requested by a person other than the person who views the display screen, in different display modes.

It is preferable that the unread management unit displays the status of the medical examination process, which is requested by a person belonging to a group to which a person who views the display screen belongs, and the status of the medical examination process, which is requested by a person belonging to a group to which the person who views the display screen does not belong, in different display modes.

It is preferable that the unread management unit displays the status of the medical examination process requested by a person who views the display screen, the status of the medical examination process requested by a person who is other than the person who views the display screen and who belongs to a group to which the person who views the display screen belongs, and the status of the medical examination process requested by a person belonging to a group to which the person who views the display screen does not belong, in different display modes.

It is preferable that the unread management unit displays the status of the specific medical examination process having a setting indicating important and the status of the medical examination process not having the setting in different display modes.

It is preferable that the unread management unit displays the status according to presence or absence of a specific mark attached to the medical examination process.

It is preferable that the display screen comprises an unread number display field for displaying the number of medical examination processes whose status is unread or revised for each patient.

It is preferable that the unread management unit acquires a part or entirety of the status from other apparatuses or systems that cooperate with the medical examination support apparatus.

It is preferable that the unread management unit changes the status to read in a case where either a requester of the medical examination process whose status is unread or revised or a person other than the requester views the medical examination process whose status is unread or revised.

It is preferable that the unread management unit changes the status to read in a case where the medical examination process whose status is unread or revised is viewed by a specific person.

It is preferable that the unread management unit changes the status to read in a case where an operation input to change the status of the medical examination process whose status is unread or revised to read is received.

It is preferable that, in a case where the display screen generation unit generates or edits a timeline display screen for displaying the medical examination process in time series for one specific patient, the unread management unit displays the status of the medical examination process on the timeline display screen.

It is preferable that, in a case where the display screen generation unit generates or edits a layout screen for displaying the medical examination process side by side on one screen for one specific patient, the unread management unit displays the status of the medical examination process on the layout screen.

It is preferable to further comprise a notification unit that provides notification of a change of the status to unread or revised in a case where the display screen is not displayed on a display unit.

It is preferable to further comprise a medical record writing unit that writes a content of the medical examination process whose status has been changed to read in an electronic medical record in a case where the status is changed to read.

The medical examination support apparatus of the invention can reduce the oversight of a medical examination process that has been revised by alerting that there has been a revision in the medical examination process.

BRIEF DESCRIPTION OF THE DRAWINGS

FIG. 7 is a diagram showing an initial screen.

FIG. 8 is a diagram showing a clinical flow screen.

FIG. 9 is a partially enlarged view of the clinical flow screen.

FIG. 15 is a diagram showing a timeline screen.

FIG. 21 is a diagram showing a medical examination support apparatus having a medical record writing unit.

DESCRIPTION OF THE PREFERRED EMBODIMENTS

First Embodiment

Figure 1:
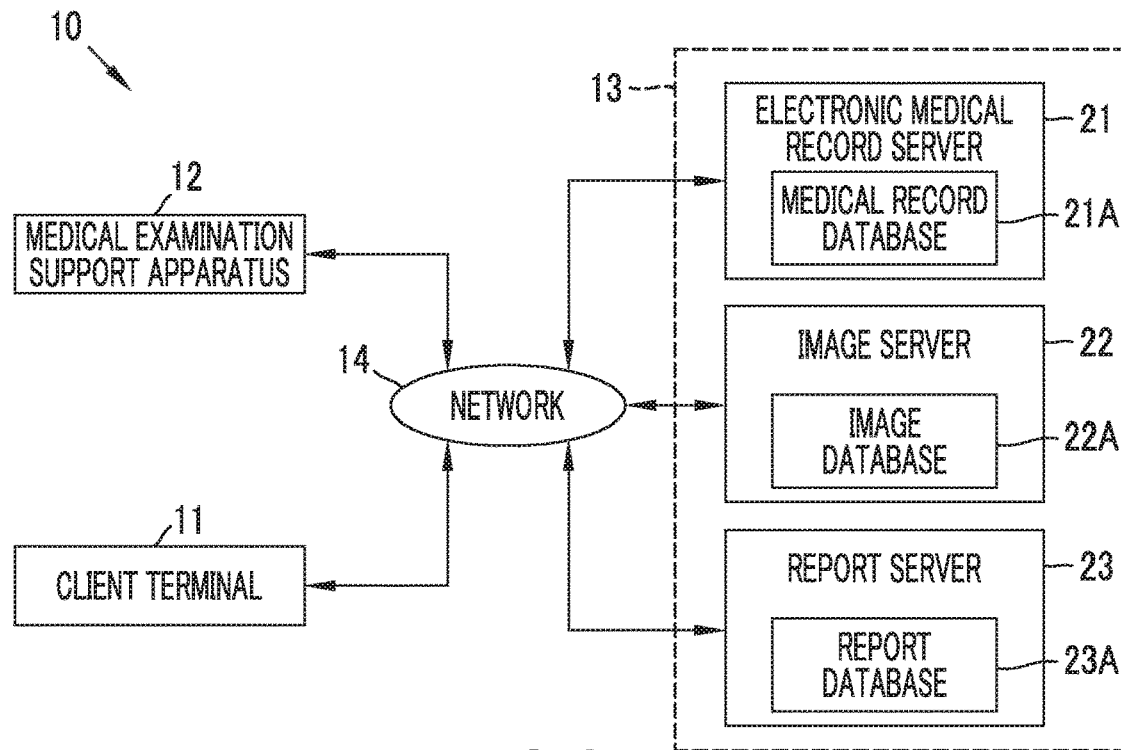
FIG. 1 is an explanatory diagram showing the configuration of a medical examination support system.

As shown in FIG. 1, a medical examination support system 10 is a computer system that performs medical examination support in a medical facility, such as a hospital, and comprises a client terminal 11, a medical examination support apparatus 12, and a server group 13. The respective elements configuring the medical examination support system 10 are communicably connected to each other using a network 14, such as a local area network (LAN) provided in a medical facility.

Figure 2:
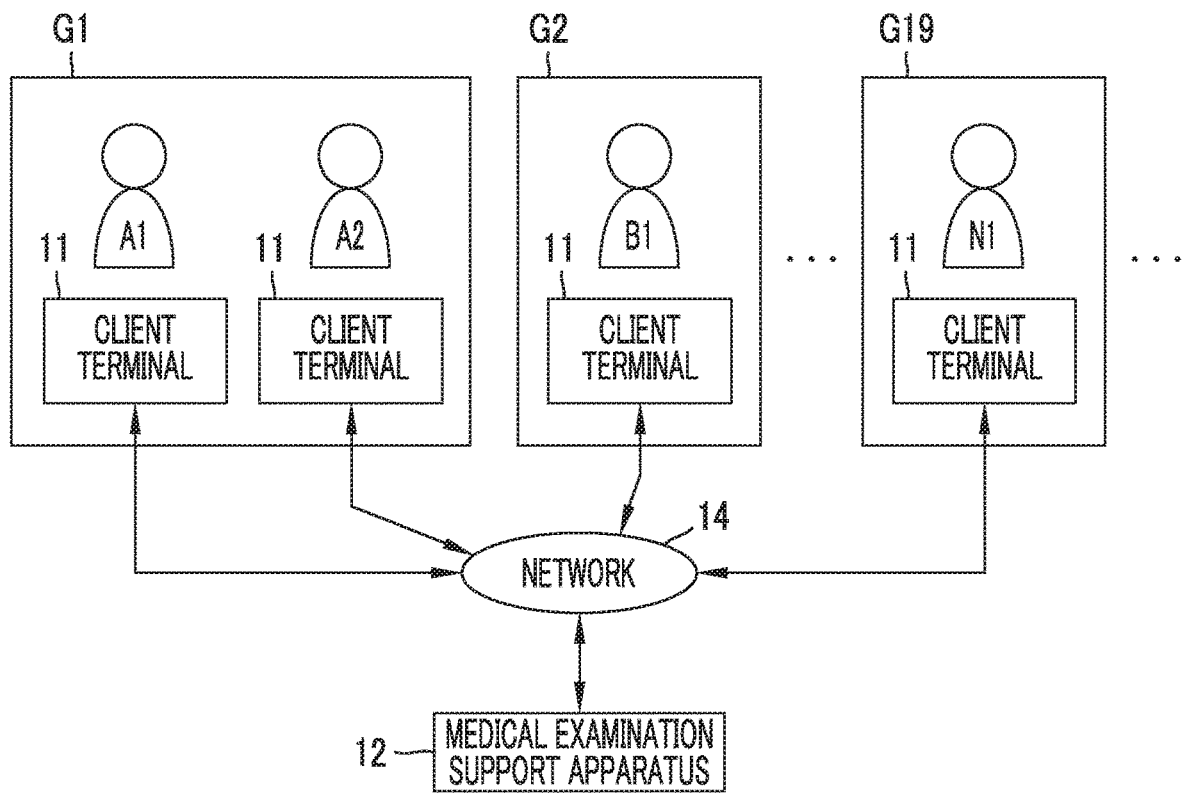
FIG. 2 is an explanatory diagram showing a client terminal provided in the medical examination support system.

The client terminal 11 is a terminal for receiving provision of a service from the medical examination support apparatus 12 (provision of a function of the medical examination support apparatus 12), and is a computer (including a case of a tablet terminal or the like) directly operated by the medical staff member, such as a doctor, a laboratory technician, or a nurse. The client terminal 11 is installed in a medical department such as internal medicine or surgery, various examination departments such as a radiological examination department or a clinical examination department, a nurse center, or other necessary places. In addition, the client terminal 11 can be provided for each medical staff member, and can be shared by a plurality of medical staff members. Therefore, as shown in FIG. 2, the medical examination support system 10 includes a plurality of client terminals 11. For example, a group G1 is the "internal medicine" to which a doctor A1 and a doctor A2 belong, and the doctor A1 and the doctor A2 each have the client terminal 11. Similarly, for example, a group G2 is the "surgery" to which a doctor B1 belongs, and the group G2 includes at least one client terminal 11. In addition, for example, a group G19 is a "radiology department" to which a technician N1 belongs, and the group G19 includes at least one client terminal 11.

The medical examination support apparatus 12 provides a display screen, which includes medical examination data (for example, an image itself) and/or information indicating the location of medical examination data (for example, a link to an image), to the client terminal 11 in response to a request from the client terminal 11, for example. The medical examination data is images, reports, and examination results acquired or created during medical practices, examinations, surgery, and the like, data obtained in the processes of other medical examinations or as results of the medical examinations, or information indicating the locations thereof (so-called link (alias) or the like). The medical examination support apparatus 12 acquires medical examination data to be used on the display screen from the server group 13.

The display screen provided to the client terminal 11 by the medical examination support apparatus 12 refers to data used by the client terminal 11 to form a screen of a display unit 36 (refer to FIG. 3) of the client terminal 11. On the display screen provided to the client terminal 11 by the medical examination support apparatus 12, not only data for full screen display in which the client terminal 11 configures display of the entire screen but also data configuring display relevant to a part of the screen is included. For example, in the present embodiment, the medical examination support apparatus 12 provides the client terminal 11 with a display screen that can be displayed in a general window form in a part of the screen of the display unit 36.

Specifically, the display screen provided to the client terminal 11 by the medical examination support apparatus 12 is a clinical flow screen 81 (refer to FIG. 8), a timeline screen 201 (refer to FIG. 15), a layout screen 301 (refer to FIG. 16), an unread data list screen 401 (refer to FIG. 18), and the like. The clinical flow screen 81 is a display screen on which identification information of a patient and a part or entirety of a medical examination process are displayed so as to be associated with each other for each of a plurality of patients. The identification information of a patient is, for example, the patient's name, date of birth, age, and sex or identification data (ID), such as a unique number and/or symbol assigned to the patient, (hereinafter, referred to as a patient ID). The medical examination process refers to the process or result of the medical examination already performed and the medical examination scheduled to be performed in the future. Therefore, the medical examination process may include not only the medical examination data already acquired but also the medical examination data scheduled to be acquired. The medical examination data scheduled to be acquired is, for example, information regarding the presence or absence of an order of a specific examination, the scheduled date and time, and the type of medical examination data scheduled to be acquired. In the present embodiment, in a case where one medical examination process includes a plurality of items (items of an examination result and the like), the medical examination process does not refer to the entire medical examination process (a collection of a plurality of items) but refers to any of the items configuring the medical examination process. The timeline screen 201 is a display screen for displaying, for one specific patient, a part or entirety of the medical examination process of the patient in time series on one screen. The layout screen 301 is a display screen on which, for one specific patient, a part or entirety of the medical examination process of the patient is displayed side by side vertically and horizontally (for example, side by side in a tile shape). The unread data list screen 401 is a display screen for displaying a list of medical examination data whose contents have not been checked by the medical staff member and/or medical examination data to be acquired in the future.

The medical examination support apparatus 12 provides a display screen to the client terminal 11 in a description format using a markup language, such as an extensible markup language (XML) data, for example. The client terminal 11 displays a display screen in the XML format using a web browser. The medical examination support apparatus 12 can provide the client terminal 11 with a display screen in another format, such as JavaScript (registered trademark) object notation (JSON), instead of the XML.

The server group 13 searches for medical examination data in response to a request from the medical examination support apparatus 12, and provides the medical examination support apparatus 12 with the medical examination data corresponding to the request. The server group 13 includes an electronic medical record server 21, an image server 22, a report server 23, and the like.

The electronic medical record server 21 has a medical record database 21A that stores electronic medical records. The electronic medical record is a collection of one or a plurality of pieces of medical examination data. Specifically, the electronic medical records include medical examination data, such as medical practice records, results of sample examinations, patient's vital signs, orders of an examination and the like, treatment records, and accounting data, for example. The electronic medical records can be input and viewed using the client terminal 11.

The medical practice record is a record of the content and the result of an inquiry or palpation or the name of a disease. A sample is blood, tissue, or the like collected from a patient, and the sample examination is a blood test, a biochemical test, or the like. The vital signs are data indicating the condition of a patient, such as the patient's pulse, blood pressure, or body temperature. The orders of an examination and the like are requests for an examination such as a sample examination, imaging using various modalities, creation of a report, treatment or surgery, medication, and the like. The treatment records are records of treatment, surgery, medication, and the like. The accounting data is data regarding a medical examination fee, a medicine fee, a hospitalization fee, and the like.

The image server 22 is a so-called picture archiving and communication system (PACS) server, and has an image database 22A that stores an examination image. The examination image is an image obtained by each of various image examinations, such as a computed tomography (CT) examination, a magnetic resonance imaging (MRI) examination, an X-ray examination, an ultrasound examination, and an endoscope examination. These examination images are recorded in a format based on the digital imaging and communications in medicine (DICOM) standard, for example. The examination image can be viewed using the client terminal 11.

The report server 23 has a report database 23A that stores an interpretation report. The interpretation report (hereinafter, simply referred to as a report) is a report that summarizes the interpretation results of examination images obtained by image examinations. The interpretation of an examination image is performed by a radiologist. A report can be created and/or viewed using the client terminal 11.

Each of the electronic medical record, the examination image, and the report described above includes a patient ID. In addition to the patient ID, the electronic medical record includes information for identifying the medical staff member, who has input medical examination data, for each piece of medical examination data. In addition to the patient ID, the examination image includes information for identifying the medical staff member (specifically, a laboratory technician) who has performed the examination. The report includes information for identifying the medical staff member (specifically, a radiologist) who has created the report. The information for identifying the medical staff member is the name of the medical staff member or an ID, such as a unique number and/or symbol assigned to each medical staff member (hereinafter, referred to as a medical staff ID).

Each of the client terminal 11, the medical examination support apparatus 12, and the servers 21 to 23 that configure the server group 13 is configured by installing an operating system program and an application program, such as a server program or a client program, on a computer as a base, such as a server computer, a personal computer, or a workstation. That is, the basic configurations of the client terminal 11, the medical examination support apparatus 12, and the servers 21 to 23 that configure the server group 13 are the same, and each of the client terminal 11, the medical examination support apparatus 12, and the servers 21 to 23 that configure the server group 13 comprises a central processing unit (CPU), a memory, a storage, a communication unit, and a connection circuit for connecting these to each other. The communication unit is a communication interface (LAN port or the like) for connection with the network 14. The connection circuit is, for example, a motherboard for providing a system bus and/or a data bus and the like.

Figure 3:
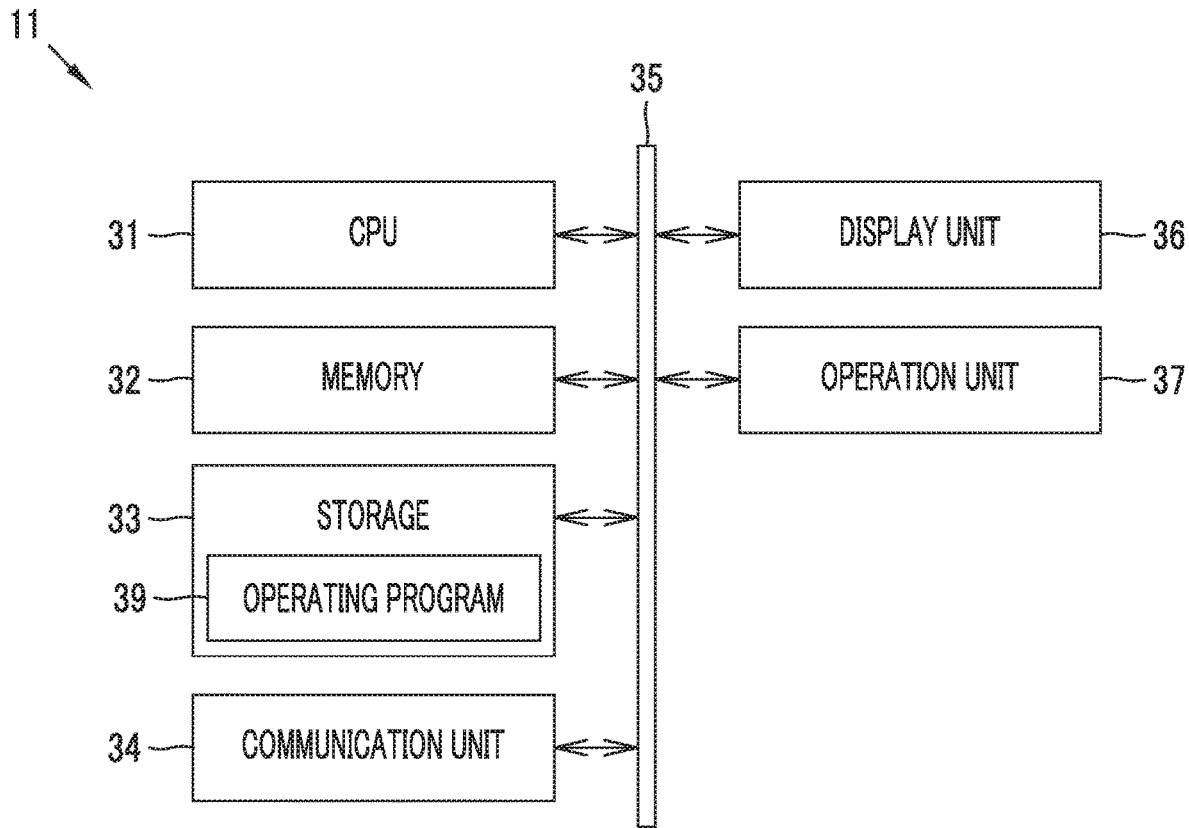
FIG. 3 is a block diagram showing the configuration of the client terminal.

As shown in FIG. 3, the client terminal 11 comprises a CPU 31, a memory 32, a storage 33, a communication unit 34, a connection circuit 35, the display unit 36, and an operation unit 37. The display unit 36 is a display using, for example, liquid crystal, and has a screen for displaying at least a display screen provided by the medical examination support apparatus 12. The operation unit 37 is, for example, a pointing device such as a mouse and/or an input device such as a keyboard. The display unit 36 and the operation unit 37 can configure a so-called touch panel.

In addition to the operating system program and the like, the client terminal 11 stores an operating program 39 in the storage 33. The operating program 39 is an application program for receiving the provision of the function of the medical examination support apparatus 12 using the client terminal 11. In the present embodiment, the operating program 39 is a program of a web browser. However, the operating program 39 can be a dedicated application program for receiving the provision of the function of the medical examination support apparatus 12. The operating program 39 may include one or a plurality of gadget engines for controlling a part or entirety of the display screen provided by the medical examination support apparatus 12. The gadget engine is a subprogram that realizes various functions by being operated in conjunction with a web browser or the like.

Figure 4:
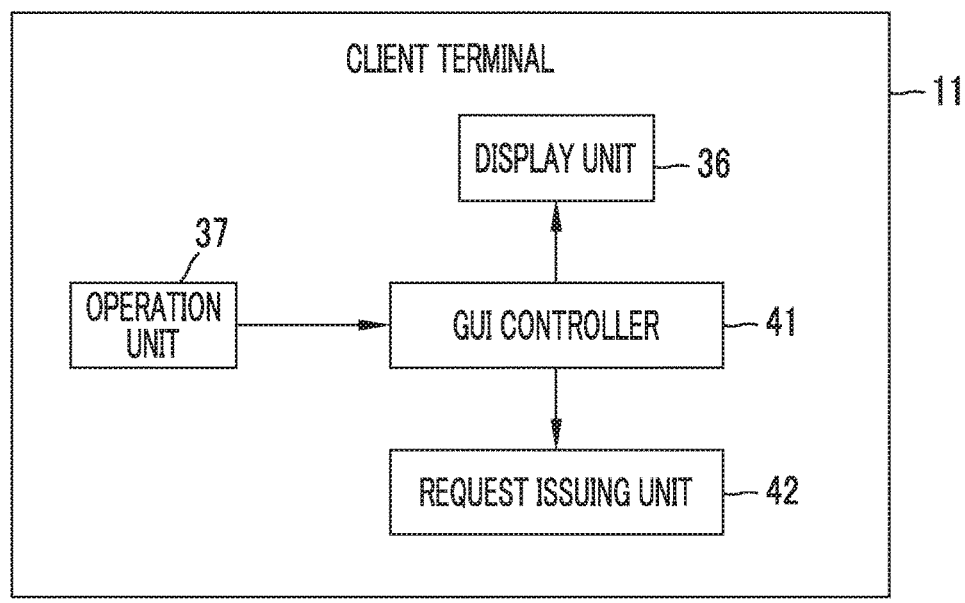
FIG. 4 is a block diagram showing the function of the client terminal.

In a case where the operating program 39 is activated in the client terminal 11, as shown in FIG. 4, the CPU 31 of the client terminal 11 cooperates with the memory 32 to function as a graphical user interface (GUI) controller 41 and a request issuing unit 42.

The GUI controller 41 displays a display screen provided by the medical examination support apparatus 12 on the web browser in the display unit 36. The GUI controller 41 controls the client terminal 11 according to an operation instruction that is input using the operation unit 37, such as a button clicking operation using a pointer.

The request issuing unit 42 issues a request (hereinafter, referred to as a processing request) for various processes with respect to the medical examination support apparatus 12 according to an operation instruction of the operation unit 37. The processing request issued by the request issuing unit 42 is, for example, a display screen distribution request or a display screen editing request. The request issuing unit 42 transmits a processing request to the medical examination support apparatus 12 through the communication unit 34 and the network 14.

The display screen distribution request is for requesting the medical examination support apparatus 12 to distribute a display screen having a specific configuration. For example, any of the clinical flow screen 81, the timeline screen 201, the layout screen 301, the unread data list screen 401, and the like can be designated and distributed in response to the display screen distribution request.

The display screen editing request is for requesting the medical examination support apparatus 12 to edit the content of medical examination data and the like to be displayed on the display screen after receiving the distribution of the display screen having a specific configuration from the medical examination support apparatus 12. For example, in the case of receiving the distribution of the clinical flow screen 81, a request for designation or change of a list of patients to be displayed, a request for designation or change of a display target period of the medical examination process, a request for designation or change of the medical examination process to be displayed, or a request for sorting the display content is the display screen editing request.

The display screen distribution request and/or the display screen editing request and the like include information, such as a medical staff ID and the address of the client terminal 11 on the network. The medical staff ID is input on the login screen (not shown) to the medical examination support system 10 (or the medical examination support apparatus 12).

Figure 5:
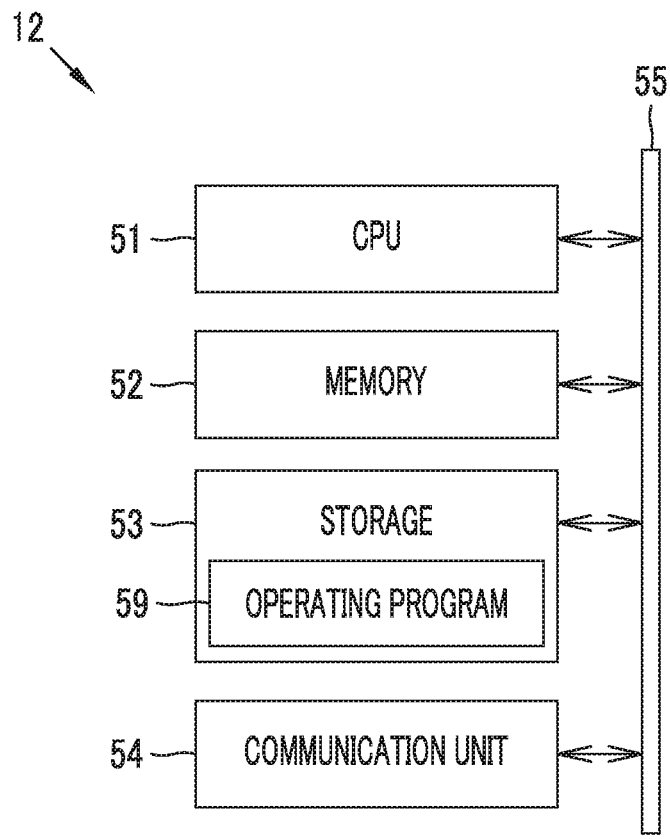
FIG. 5 is a block diagram showing the configuration of a medical examination support apparatus.

As shown in FIG. 5, the medical examination support apparatus 12 comprises a CPU 51, a memory 52, a storage 53, a communication unit 54, and a connection circuit 55. The medical examination support apparatus 12 can comprise a display unit and/or an operation unit as necessary similarly to the client terminal 11. In the present embodiment, the medical examination support apparatus 12 does not have a display unit and an operation unit although the display unit and/or the operation unit can be attached as necessary.

Figure 6:
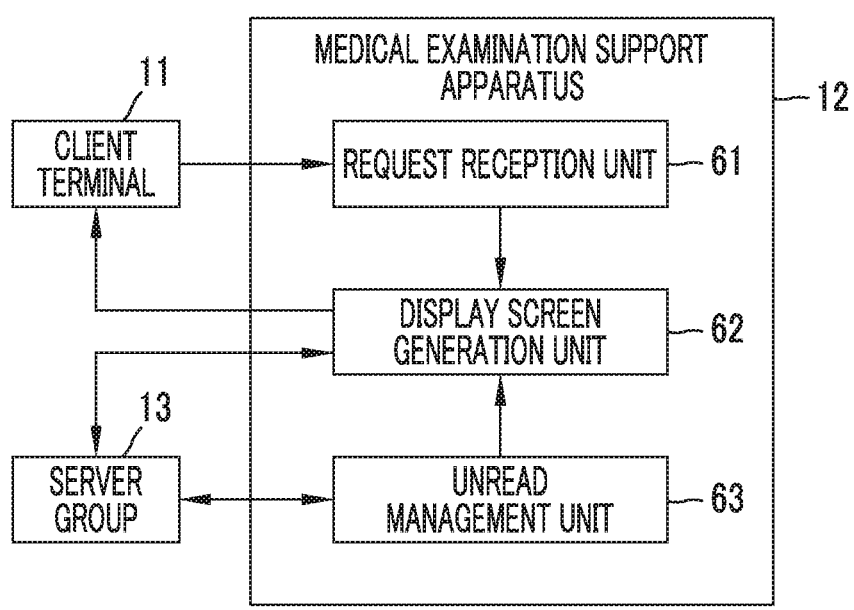
FIG. 6 is a block diagram showing the function of the medical examination support apparatus.

In addition to the operating system program and the like, the medical examination support apparatus 12 stores an operating program 59 in the storage 53. The operating program 59 is an application program for making a computer configuring the medical examination support apparatus 12 function as the medical examination support apparatus 12. In a case where the operating program 59 is activated, as shown in FIG. 6, the CPU 51 of the medical examination support apparatus 12 cooperates with the memory 52 to function as a request reception unit 61, a display screen generation unit 62, an unread management unit 63, and the like.

The request reception unit 61 receives various processing requests, such as a display screen distribution request and a display screen editing request, from the client terminal 11. In a case where the request reception unit 61 receives various processing requests, the request reception unit 61 inputs a processing instruction to each unit, which performs the corresponding processing, according to the content of the requested processing. For example, in a case where there is a display screen distribution request from the client terminal 11, the request reception unit 61 inputs an instruction to generate the corresponding display screen to the display screen generation unit 62. Similarly, in a case where there is a display screen editing request from the client terminal 11, the request reception unit 61 inputs an instruction to edit the corresponding display screen to the display screen generation unit 62. The request reception unit 61 also receives a request for login to the medical examination support apparatus 12, and a login processing unit (not shown) performs login processing, such as checking of a medical staff ID and a password.

Figure 7:
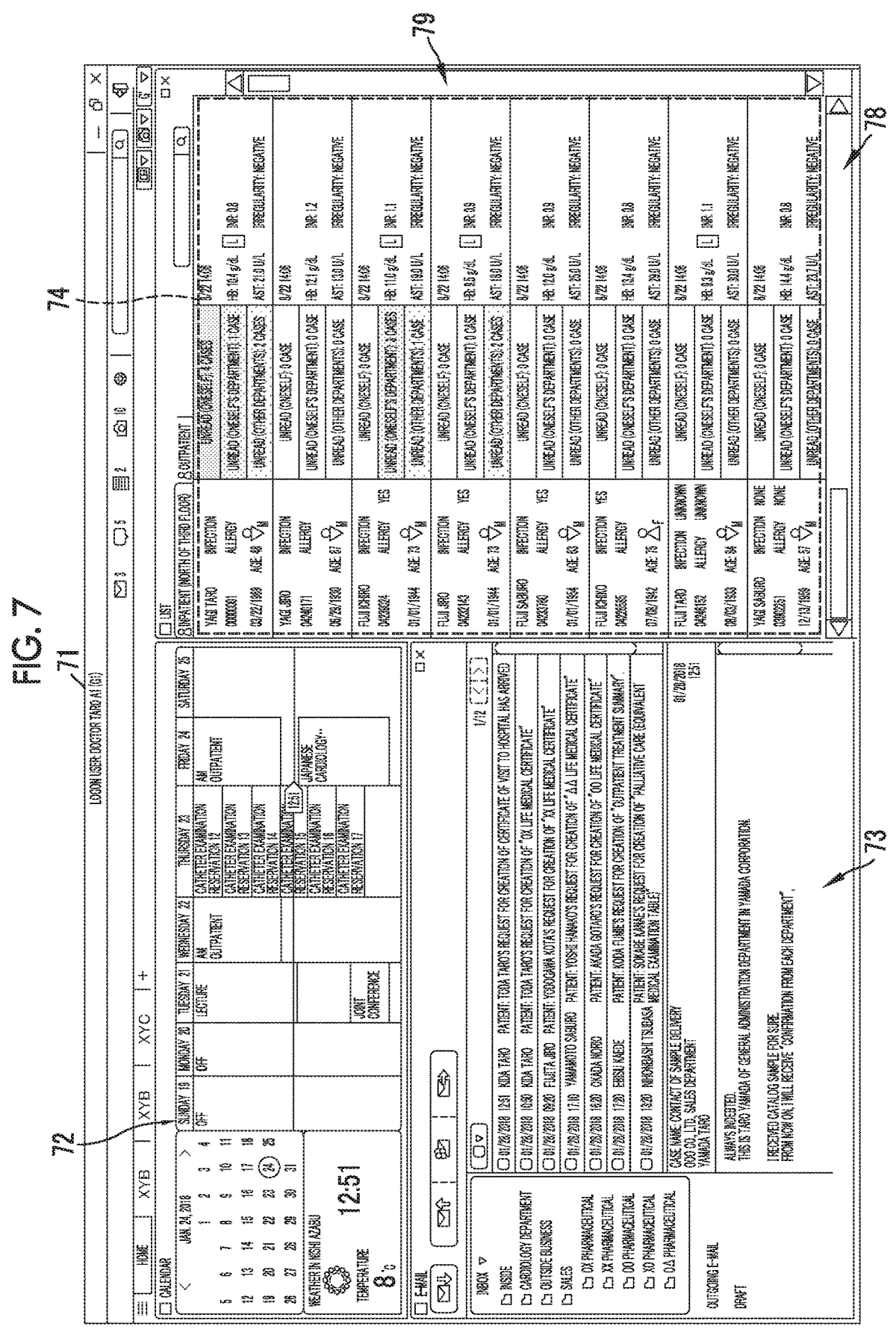

The display screen generation unit 62 generates or edits various display screens, such as the clinical flow screen 81. In the present embodiment, in a case where there is a new display screen distribution request, a display controller 66 generates XML data indicating the display screen. In a case where there is a display screen editing request, the display controller 66 edits previously created XML data according to the request content. The display screen generation unit 62 accesses the server group 13 as necessary, and acquires information regarding the medical examination process and the like used for generation or editing of the display screen. In order to reduce the frequency of access to the server group 13, the display screen generation unit 62 can hold some or all of the pieces of information regarding the medical examination process and the like acquired from the server group 13. In a case where the login processing unit normally completes the login processing, the display screen generation unit 62 generates an initial screen 71 (refer to FIG. 7) to be displayed first after login. At the time of creating or editing the initial screen 71, the display screen generation unit 62 acquires information required for generation or editing of the initial screen 71 from the server group 13, the client terminal 11, or other apparatuses or systems that cooperate with the medical examination support system 10.

The unread management unit 63 manages the status of the medical examination process included in the display screen generated or edited by the display screen generation unit 62. The status of the medical examination process is management information indicating that the medical examination process has been unread, or management information indicating that the medical examination process has been read, or management information including both the pieces of information. "Unread (management information including unread)" refers to a state in which the medical staff member has not yet performed predetermined processing to be performed, such as viewing, editing, comment insertion, and approval processing (hereinafter, referred to as "viewing and the like"), in association with the medical examination process. "Read (management information including read)" refers to a state in which the medical staff member has performed predetermined processing to be performed, such as viewing and the like, in association with the medical examination process. The management information including both the pieces of information of unread and read is substantially unread or read management information. Since unread and read indicate an alternative state, unread is simultaneously an indication of not being read and read is simultaneously an indication of not being unread.

In addition to unread, read, or both, the unread management unit 63 manages the status of "revised" as one of the statuses of the medical examination process. "Revision" is a status indicating that there has been a change in the content of the unread or read medical examination process. For example, revision of an examination image refers to adding a newly acquired examination image to an already acquired examination image or replacing some or all of the already acquired examination images with newly acquired examination images. Revision of a report refers to adding information, such as findings, to an existing report, changing the content of an existing report, and the like.

In addition to the above, the unread management unit 63 manages the status of "important" as one of the statuses of the medical examination process. The "important" is a status indicating a medical examination process in which the medical staff member has set (for example, set an important flag) to draw attention to the medical examination process for himself or herself or other medical staff members. The unread management unit 63 can manage the status of "important" as an alternative status with respect to unread, read, and revised, or can manage the status of "important" as a status that can coexist with the statuses of unread, read, and revised. Being an alternative to unread and the like refers to setting and managing any one of unread, read, revised, or important for one medical examination process. Being able to coexist with unread and the like refers to setting and managing two or more of unread, read, or revised, and important, for example, managing a certain medical examination process with unread and important.

The unread management unit 63 displays the above-described status on the display screen generated or edited by the display screen generation unit 62. Therefore, the unread management unit 63 can reduce the oversight of the medical examination process by the medical staff member. For example, on the display screen generated or edited by the display screen generation unit 62, the unread management unit 63 attaches a predetermined mark (for example, a "badge" in a predetermined form) indicating a status, such as unread or read, to a display portion of the medical examination process as a target. That is, the unread management unit 63 displays a status, such as unread, on the display screen according to the presence or absence or the form of a specific mark attached to the medical examination process. The display using a mark is easy to understand visually, and in particular, helps to achieve the goal of reducing oversight. The form of a mark is the shape (including a difference in size), color, or pattern of a mark or a combination thereof.

In the present embodiment, since the display screen generation unit 62 generates or edits XML data indicating the display screen, the unread management unit 63 edits the XML data generated or edited by the display screen generation unit 62 or causes the display screen generation unit 62 to edit the XML data generated or edited by the display screen generation unit 62 (including a case of causing the display screen generation unit 62 to edit the XML data at the same time as the generation of the display screen). As a result, a medical examination process to be marked and the color and the form of a mark to be attached are designated, or a medical examination process with an already attached mark that is to be removed (or a medical examination process without a mark) is designated. In this manner, the unread management unit 63 displays a status, such as unread, on the display screen generated by the display screen generation unit 62.

In particular, in a case where there is a revision in the medical examination process whose status is unread or read, the unread management unit 63 displays the status of the medical examination process that has been revised in a display mode different from the display mode of unread or read. Therefore, the unread management unit 63 provides the user of the client terminal 11 with information indicating that the medical examination process has been revised so as to be distinguished from unread and read.

In the present embodiment, for example, the unread management unit 63 attaches a mark indicating unread and the like for unread and the like and additionally attaches a mark indicating important for the medical examination process having a setting indicating important, thereby performing display in a state in which a status, such as unread, and a status, such as important, can coexist. Therefore, the unread management unit 63 displays the status of a specific medical examination process having a setting indicating important and the status of a medical examination process not having a setting indicating important in different display modes on the display screen so that the statuses are distinguished from each other. As a result, the unread management unit 63 can reduce the oversight of the medical examination process having a setting indicating important.

For example, the unread management unit 63 acquires the status of unread, read, revised, and/or important from an apparatus or a system that cooperates with the medical examination support apparatus 12, such as the server group 13. In addition, the unread management unit 63 can acquire the statuses of unread, read, revised, and/or important directly from the client terminal 11 by acquiring the operation information of the client terminal 11.

The display screen generation unit 62 distributes the display screen generated or edited as described above to the client terminal 11 through the communication unit 54. Accordingly, the client terminal 11 displays the display screen provided from the display screen generation unit 62 on the display unit 36. In a case where the unread management unit 63 further edits the display screen generated or edited by the display screen generation unit 62 in order to display marks of unread and the like on the display screen, the unread management unit 63 can provide the display screen to the client terminal 11.

The unread management unit 63 manages the number of statuses of unread, read, revised, and/or important to be displayed on the display screen. In addition, the unread management unit 63 displays the number of statuses on the display screen as necessary. In the present embodiment, a sum of the number of unread cases and the number of revised cases is managed as an unread number and displays on the display screen.

In addition, the unread management unit 63 can manage the statuses of unread, read, revised, and/or important so as to be distinguished for each requester of the medical examination process, and can display the statuses of unread, read, revised, and/or important on the display screen in display modes that can be distinguished for each requester. The distinction between requesters of the medical examination process includes not only distinction between medical staff members but also distinction according to a group (medical department or the like) to which the medical staff member belongs. In the present embodiment, the statuses of unread, read, revised, and/or important are managed so as to be distinguished for each requester, and are displayed on the display screen in display modes that can be distinguished for each requester. In the present embodiment, requesters of the medical examination process are divided into three types of "oneself", "oneselfs department", and "other departments". "Oneself" indicates that the requester of the medical examination process is the user himself or herself of the client terminal 11. The user of the client terminal 11 is a person who views the display screen on the client terminal 11 using the client terminal 11. "Oneselfs department" indicates a case where the requester of the medical examination process belongs to a group to which the user of the client terminal 11 belongs and is a medical staff member other than the user of the client terminal 11. "Other departments" indicates a case where the requester of the medical examination process is a medical staff member belonging to a group to which the user of the client terminal 11 does not belong.

That is, the unread management unit 63 manages statuses, such as unread, so that "oneself", "oneselfs department", and "other departments" are distinguished. In this regard, the unread management unit 63 distinguishes between the status of the medical examination process requested by a person (oneself) who views the display screen and the status of the medical examination process requested by a person (medical staff member in oneselfs department and/or other departments) other than the person who views the display screen, and displays the statuses on the display screen in different display modes. Accordingly, the medical staff member can clearly recognize the medical examination process that the medical staff member has to view so as to be distinguished from others. As a result, the medical staff member can reduce the oversight of the medical examination process that the medical staff member has to view.

Similarly, the unread management unit 63 manages statuses, such as unread, so that "oneself", "oneselfs department", and "other departments" are distinguished. In this regard, the unread management unit 63 distinguishes between the status, such as unread, of the medical examination process requested by a person (medical staff member belonging to the oneselfs department (including oneself)), who belongs to a group to which a person (oneself) who views the display screen belongs, and the status, such as unread, of the medical examination process requested by a person (medical staff member belonging to other departments), who belongs to a group to which the person who views the display screen does not belong, and displays the statuses on the display screen in different display modes. Accordingly, the medical staff member can clearly recognize the medical examination process that medical staff members of the oneselfs department (including the medical staff member himself or herself) have to view so as to be distinguished from others. As a result, since the medical staff member can efficiently support or manage the tasks of medical staff members of the group, it is possible to reduce the oversight of the medical examination process in units of groups. In addition, by contacting other departments as necessary, it is possible to help reduce oversight by medical staff members in other departments. In a case where the user of the client terminal is an administrator (person in charge) of a medical facility, such as a hospital, management can be performed in the entire facility so as not to overlook the medical examination process.

Then, the unread management unit 63 manages statuses, such as unread, so that "oneself", "oneselfs department", and "other departments" are distinguished. In this regard, the unread management unit 63 distinguishes between the status, such as unread, of the medical examination process requested by a person (oneself) who views the display screen, the status, such as unread, of the medical examination process requested by a person who belongs to a group to which the person who views the display screen belongs and who is a person (medical staff member of the oneselfs department (excluding oneself)) other than the person who views the display screen, and the status, such as unread, of the medical examination process requested by a person (medical staff member belonging to other departments) belonging to a group to which the person who views the display screen does not belong, and displays the statuses on the display screen in different display modes. Therefore, since the status, such as unread, is clear in a state in which "oneself", "oneselfs department", and "other departments" are distinguished, it is possible to reduce the oversight of the medical examination process that oneself has to view. As a result, it is possible to reduce the oversight of the medical examination process in units of groups and to help reduce oversight by medical staff members in other departments.

The medical examination support system 10 configured as described above operates as follows. First, in a case where a medical staff member logs in to the medical examination support system 10 using the client terminal 11, the display screen generation unit 62 generates the initial screen 71 shown in FIG. 7 based on the setting or the like for each medical staff member and provides the initial screen 71 to the client terminal 11. Then, the client terminal 11 displays the initial screen 71 on the screen of the display unit 36.

The initial screen 71 has, for example, three display fields of a schedule display field 72, an e-mail display field 73, and a list display field 74. The display content of the schedule display field 72 and the e-mail display field 73 is generated by acquiring information from an apparatus or a system other than the client terminal 11 by the gadget engine, which is a part of the operating program 39 of the client terminal 11. In the present embodiment, the list display field 74 displays at least a part of the clinical flow screen 81. Therefore, the display screen generation unit 62 generates the initial screen 71 including the schedule display field 72 and the e-mail display field 73, which do not include the content, and the list display field 74 including the content of the clinical flow screen 81. The client terminal 11 displays the initial screen 71, on which the content of the schedule display field 72 and the e-mail display field 73 is supplemented, on the screen of the display unit 36 using the gadget engine.

In a case where all of the content to be displayed does not fit in the list display field 74, a scroll bar 78 and a scroll bar 79 for transitioning (so-called scrolling) the display content of the list display field 74 are displayed in the list display field 74 or in the vicinity of the list display field 74. The scroll bar 78 is a GUI operated to transition the display content of the list display field 74 in a horizontal direction to display a non-displayed portion. The scroll bar 79 is a GUI operated to transition the display content of the list display field 74 in a vertical direction to display a non-displayed portion. Display and control of such a GUI are performed by the GUI controller 41.

For example, in a case where a predetermined menu or the like is operated using a GUI, such as a pointer (not shown), on the initial screen 71 described above, the request issuing unit 42 issues a display screen distribution request. The operation in which the request issuing unit 42 issues a display screen distribution request based on the operation of such a GUI or the like is a display screen distribution request step. In the present embodiment, in order to display the entire clinical flow screen 81 partially displayed in the list display field 74, an operation for displaying the clinical flow screen 81 is performed. As a result, the request issuing unit 42 issues a distribution request of the clinical flow screen 81.

In a case where the request issuing unit 42 issues a display screen distribution request, the request reception unit 61 in the medical examination support apparatus 12 receives the display screen distribution request, and the display screen generation unit 62 generates a display screen according to the display screen distribution request. The operation of the display screen generation unit 62 for generating a display screen according to the display screen distribution request is a display screen generation step. In the present embodiment, the display screen generation unit 62 generates the clinical flow screen 81 using information according to the medical examination process or the like appropriately acquired from the server group 13 or the like.

As described above, in a case where the display screen generation unit 62 generates a display screen according to the distribution request, the unread management unit 63 appropriately acquires the status, such as unread, of the medical examination process, which is to be displayed on the display screen, from the server group 13 or the like before generating the display screen, or at the same time as the generation of the display screen (in parallel with the generation of the display screen), or after generating the display screen. Then, the unread management unit 63 edits the display screen generated by the display screen generation unit 62, or causes the display screen generation unit 62 to further edit the display screen generated by the display screen generation unit 62. As a result, the unread management unit 63 displays a status, such as unread, on the display screen. In the present embodiment, since the display screen generation unit 62 generates the clinical flow screen 81, the unread management unit 63 acquires the status, such as unread, of the medical examination process displayed on the clinical flow screen 81, and displays the status, such as unread, on the clinical flow screen 81. The operation of the unread management unit 63 for acquiring the status of the medical examination process, such as unread, is a status acquisition step. The operation of the unread management unit 63 for displaying the status of the medical examination process, such as unread, on the display screen generated by the display screen generation unit 62 is a status display step.

Thereafter, the GUI controller 41 of the client terminal 11 receives the distribution of the display screen generated as described above, displays the received display screen on the screen of the display unit 36 instead of the initial screen 71 or displays the received display screen in another window or the like so as to overlap the initial screen 71 while maintaining the initial screen 71.

Figure 8:
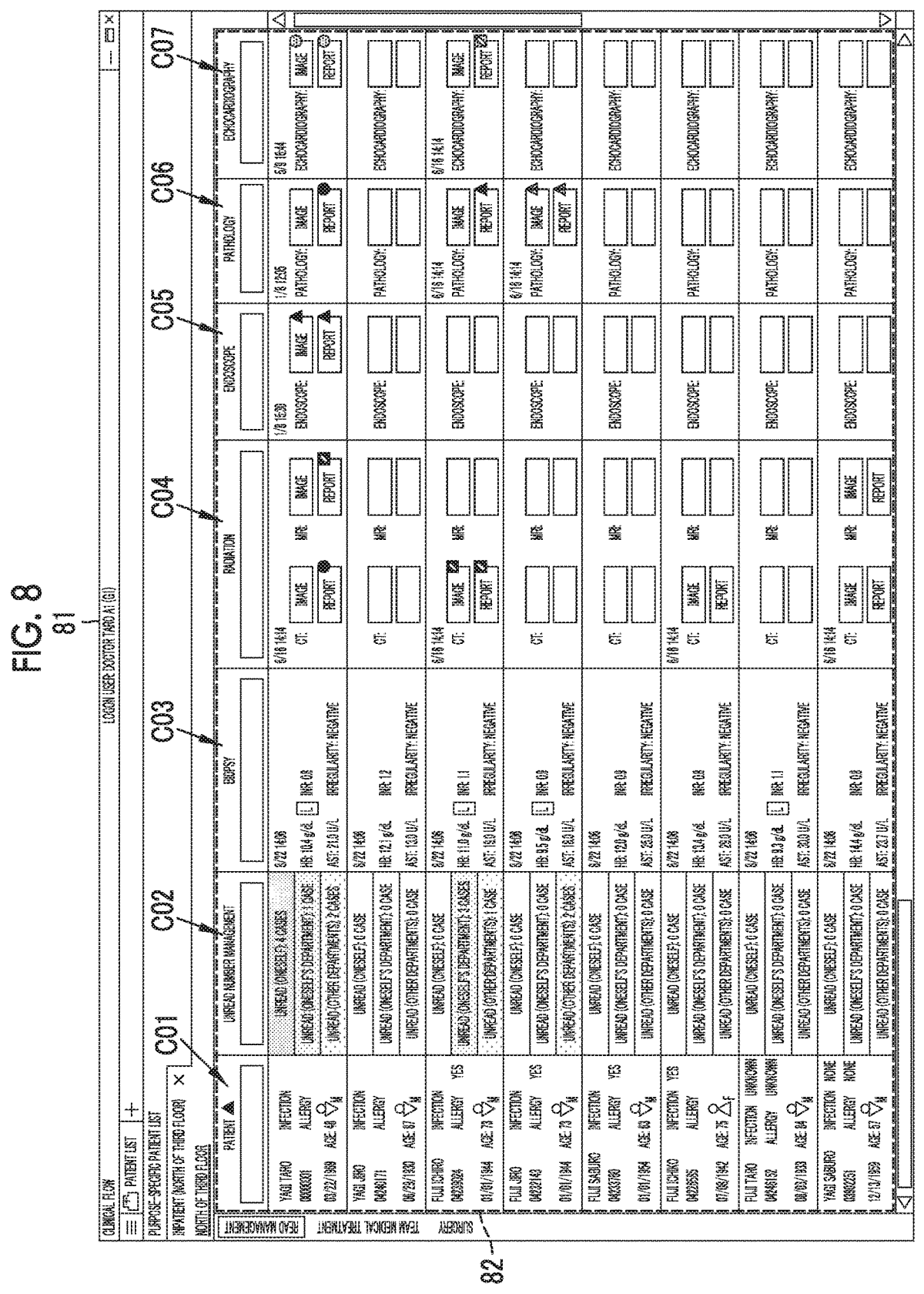

As shown in FIG. 8, the clinical flow screen 81 generated in the present embodiment comprises a clinical flow display field 82 having a patient column C01, an unread number management column C02, a biopsy column C03, a radiation column C04, an endoscope column C05, a pathological column C06, an echocardiographic column C07, and the like, for example. The patient column C01 configures a list of a plurality of patients satisfying predetermined conditions. The predetermined conditions are, for example, that a person in charge is a medical staff member who is a login user or that a person in charge is a group (medical department or the like) to which a medical staff member who is a login user belongs. The unread number management column C02 is a collection of fields for displaying the number of unread cases of the medical examination process. Each of the biopsy column C03, the radiation column C04, the endoscope column C05, the pathological column C06, the echocardiographic column C07, and the like (columns other than the patient column C01 and the unread number management column C02) is a collection of fields for displaying the process or result of each examination or the like that is the display name. Each column of the biopsy column C03, the radiation column C04, the endoscope column C05, the pathological column C06, the echocardiographic column C07, and the like (columns other than the patient column C01 and the unread number management column C02) is a medical examination process column for displaying the medical examination process. In the clinical flow display field 82, a non-displayed portion can be displayed by a scroll operation or the like, similarly to the list display field 74 on the initial screen 71.

Figure 10:
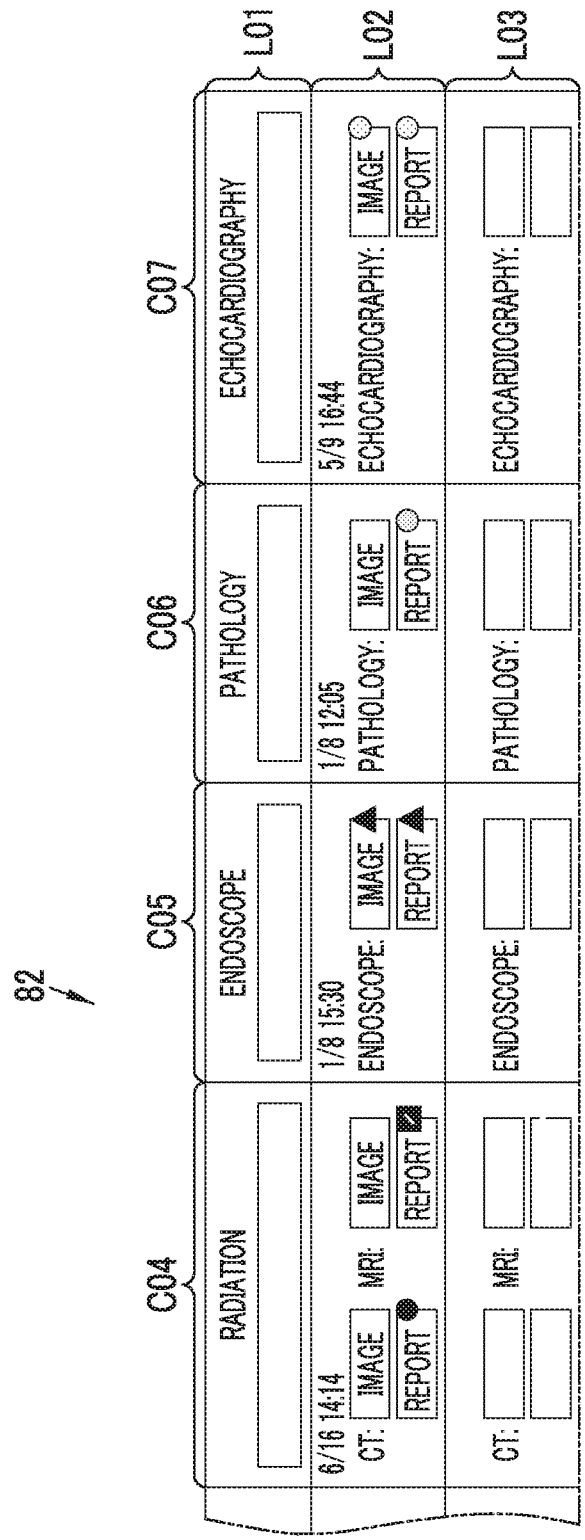
FIG. 10 is a partially enlarged view of the clinical flow screen.

As shown in FIGS. 9 and 10, the clinical flow display field 82 has an item display row L01 showing the display item of each column in the top row. By clicking the item name or the like in each field of item display row L01 with a pointer or the like, the display content can be sorted in units of rows according to descending, ascending, or other designated conditions. Sorting in units of rows refers to changing the display order while maintaining the association in the row direction. For example, in a case where "patient" is clicked in the patient column CO and the item display row L01, the request issuing unit 42 issues a display screen editing request. Then, the display screen generation unit 62 edits the clinical flow screen 81 according to predetermined conditions, such as the order of patient IDs, and provides the edited clinical flow screen 81 to the client terminal 11. As a result, the display content of the clinical flow display field 82 is sorted in the order of patient IDs or the like. In addition, a mark (for example, a "▲" mark) indicating that sorting has been performed is displayed on each item of the item display row L01 as a reference of sorting.

Second and subsequent rows in the clinical flow display field 82 configure a so-called clinical flow in which identification information of each patient is associated with the medical examination process of the patient. In FIGS. 9 and 10, clinical flows for two patients of "Yagi Taro" shown in the row L02 and "Yagi Jiro" shown in the row L03 are exemplified. The medical examination process included in the clinical flow of each patient is managed and displayed for each item (for example, medical examination data) included in each medical examination process. For example, for a radiographic image examination (radiation column C04) that is one of the medical examination process, a status such as unread is managed and displayed individually for "image" of CT, "report" of CT, "image" of MRI, and "report" of MRI. In the medical examination process field (for example, a field of a row L02 and a column of C04) of each patient, display of an "image" or a "report" indicates that the medical examination data has already been acquired. Then, no display of an "image" or a "report" indicates that the "image" or the "report" has not yet been acquired or that there is no schedule to acquire the "image" or the "report" (refer to a field of a row L03 and a column of C04). The same applies to the other medical examination process fields.

Figures 11, 12:
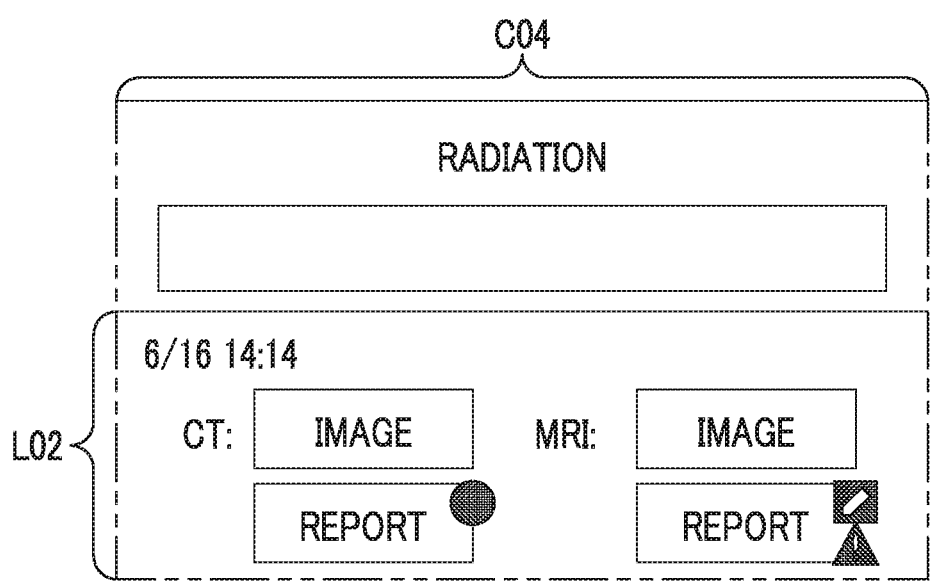
FIG. 11 is a diagram showing examples of a badge indicating a status, such as unread.
FIG. 12 is an explanatory diagram showing a badge display mode.

The status, such as unread, is displayed with a "badge", which is a mark indicating the content of the status, for each item of the medical examination process. As shown in FIG. 11, in order to display statuses, such as unread, the unread management unit 63 uses badges having different shapes and patterns for essentially new "unread" due to newly acquiring medical examination data, "revised" indicating that unread occurs again due to revision, "read" and "important". In this specification, the term "unread" simply means the above-described new unread. In the present embodiment, a round ("O") badge is attached to the item "unread". In addition, a quadrangular (" ") badge including a pattern imitating a pen is attached to an item for which "revision" has been made. A triangular ("Δ") badge including a pattern of an exclamation mark ("!") is attached to the item "important". Then, any of the above-described badges is not attached to the item "read" or these badges are removed to display that this has been read.

In addition, the status, such as unread, differs in the color of "badge", which is a mark indicating the content of the status, according to the requester of the medical examination process. Therefore, requesters of "oneself", "oneselfs department", and "other departments" are displayed according to the color of the badge. For example, the color indicating "oneself" is orange, the color indicating "oneself s department" is blue, and the color indicating "other departments" is green.

For example, in a field of row L02 and column C04 (refer to FIG. 10), an orange and round badge is attached to the item of the report of CT. For this reason, it is clear that the requester of the CT report of the patient ("Yagi Taro") is the user himself or herself of the client terminal 11 and the CT report of the patient ("Yagi Taro") is an unread report that has been newly added. In the same field, an orange and quadrangular badge is attached to the item of the report of MRI. For this reason, it is clear that the requester of the MRI report of the patient is the user himself or herself of the client terminal 11 and the mark of revised is attached since unread has occurred due to revision. In addition, in the same field, it can be seen that the examination image ("image") of CT and the examination image of MRI have already been read and there is no revision thereafter since no mark is attached thereto. The same applies to the other fields.

As shown in FIG. 12, for example, in a case where the report of MRI is a report requested by the user himself or herself of the client terminal 11, the report of MRI is unread due to revision, and the medical staff member who is the creator of the report sets "important" for the revised content, both a green quadrangular badge indicating that there has been a revision and a green triangular badge indicating that the report of MRI is important are attached. Therefore, it is clear that there has been a revision and the content is important.

As described above, in the medical examination support apparatus 12, the unread management unit 63 manages the status of the medical examination process, such as unread. Then, a status, such as unread, is displayed on the display screen, such as the clinical flow screen 81. For this reason, since the status of each medical examination process, such as unread, is clear on the display screen, such as the clinical flow screen 81, it is possible to reduce the oversight of the unread medical examination process.

In particular, the medical examination support apparatus 12 manages and displays "revised" and "unread" due to new acquisition or the like so as to be clearly distinguished. Compared with revisions for error correction, addition of content, and the like in general documents and the like in other fields, revision of the medical examination process is likely to be directly related to the treatment plan and the like after the revision and accordingly is particularly important. For this reason, in a case where there is a revision in the medical examination process, it is possible to reduce the oversight of the revised information, which is particularly important as described above, by managing and displaying the fact so as to be distinguished from other statuses.

The management and display of a status, such as unread, in the first embodiment described above is particularly useful in the case of displaying a display screen, which is viewed in common by at least the user himself or herself of the client terminal 11 and the others (medical staff members other than the user himself or herself belonging to the oneself's department or medical staff members in other departments), on the screen. This is because, in addition to the medical examination process requested by oneself, the medical examination process requested by the others is displayed on the display screen, such as the clinical flow screen 81.

Figure 13:
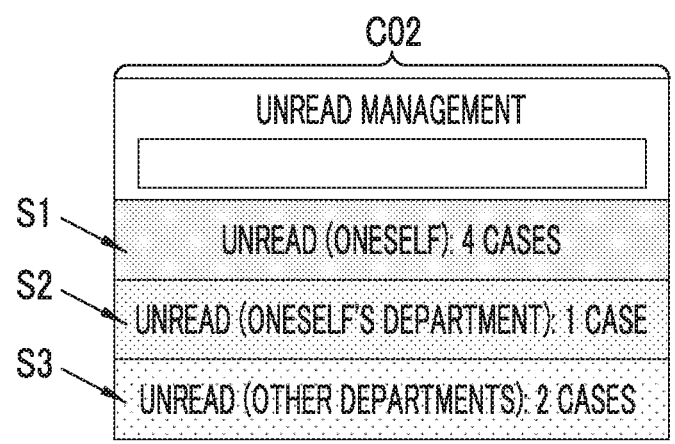
FIG. 13 is an enlarged view of an unread management field on the clinical flow screen.
Figure 14:
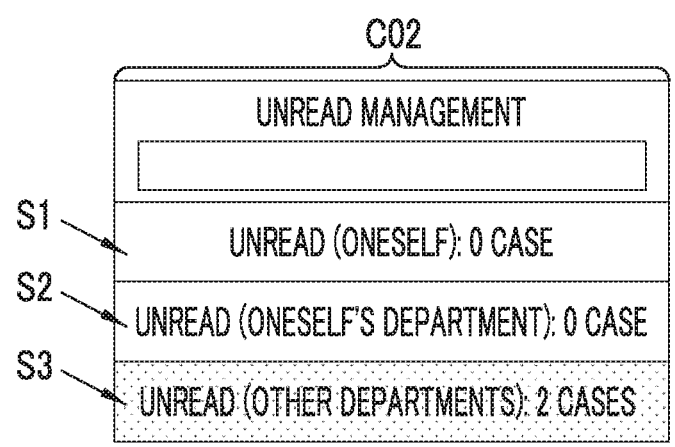
FIG. 14 is an enlarged view of an unread management field on the clinical flow screen.

In the first embodiment, the clinical flow screen 81 that is one of display screens has a field of unread number management column C02 (hereinafter, referred to as an unread number display field) of each patient, such as a field of row L02 and column C02 (refer to FIG. 9), for example. In a case where the unread number display field is provided, it is possible to immediately recognize the presence or absence of an unread or revised medical examination process without checking the entire clinical flow by scrolling or the like. As a result, it is easy to further reduce the oversight of the unread or revised medical examination process. The unread number display field displays, for example, the number (number of cases) of medical examination processes whose statuses are unread or revised for each patient. In the present embodiment, the unread number display field is divided into three rows. For example, as shown in FIG. 13, the number of unread or revised cases of "oneself" is displayed in the first row S1, the number of unread or revised cases of "oneselfs department" is displayed in the second row S2, and the number of unread or revised cases of "other departments" is displayed in the third row S3. Each of the rows S1 to S3 has the same color as the badge in a case where the displayed number of cases is one or more. For example, in a case where the number of cases displayed in the first row S is one or more, the first row S1 is colored in orange similarly to the badge indicating unread or revised of "oneself". Therefore, without checking the entire clinical flow by scrolling or the like, it is possible to distinguish "oneself", "oneselfs department", and "other departments" from each other, and it is possible to immediately recognize the presence or absence of an unread or revised medical examination process in each category. As a result, it is particularly easy to reduce the oversight of the unread or revised medical examination process. In a case where the displayed number of cases is zero, as shown in FIG. 14, each of the rows S1 to S3 is not colored. This is to make the row to be colored relatively noticeable.

In the first embodiment, the shape of the badge is changed based on a status such as unread, and the color of the badge is changed based on the category of the requester (refer to FIG. 11). However, the color of the badge may be changed based on a status such as unread, and the shape of the badge may be changed based on the category of the requester. The form of the badge may be changed for each combination of a status, such as unread, and a category of the requester. Needless to say, a badge for displaying the status of read may be provided. Any form of the badge can be adopted as long as respective sections can be distinguished by the form. The same applies to the setting of the display color of the unread number display field.

In the first embodiment described above, a status, such as unread, is displayed on the display screen using a badge (refer to FIG. 11). However, a status, such as unread, may be displayed by changing the display mode of the medical examination process itself instead of attaching a badge to the medical examination process or in addition to attaching a badge. For example, a status, such as unread, may be displayed by changing the font type, font size, font color, and background color of the characters of an "image" according to the status, such as unread.

Second Embodiment

In the first embodiment described above, the status of the medical examination process, such as unread, is displayed on the clinical flow screen 81. However, as shown in FIG. 15, in a case where the display screen generation unit 62 generates or edits the timeline screen 201, the unread management unit 63 can display the status of the medical examination process, such as unread, on the timeline screen 201 similarly to the clinical flow screen 81 in the first embodiment.

On the timeline screen 201, time elements, such as date and time, and the medical examination process are displayed so as to be associated with each other. For example, in FIG. 15, it is displayed in the column of "18/06/12" (Jun. 12, 2018) that there was a CT examination. In this case, for example, the unread management unit 63 displays a status, such as unread, on the timeline screen 201 by attaching the same badge (refer to FIG. 11) as the clinical flow screen 81 in the first embodiment to the display of "image" indicating a CT examination image or "repo" indicating a report. In FIG. 15, a green quadrangular badge indicating "revised" is attached to the CT report ("repo").

As described above, in the case of displaying the status of the medical examination process, such as unread, on the timeline screen 201, the date and time at which the medical examination process was performed or the date and time at which the medical examination process is to be scheduled can be grasped in association with the status such as unread. For example, in the case of performing the same kind of medical examination process a plurality of times, it is useful to be able to grasp a status, such as unread, so that the medical examination process of each time can be distinguished. In addition, in a case where there has been a revision after a certain amount of time since the medical examination process was performed first, even in a case where notification using e-mail or the like is provided, it is not easy to visually know that the past medical examination process has been revised on another display screen. However, by displaying the status of the revision on the timeline screen 201, revision of the past medical examination process can also be grasped easily and reliably.

Third Embodiment

Figure 16:
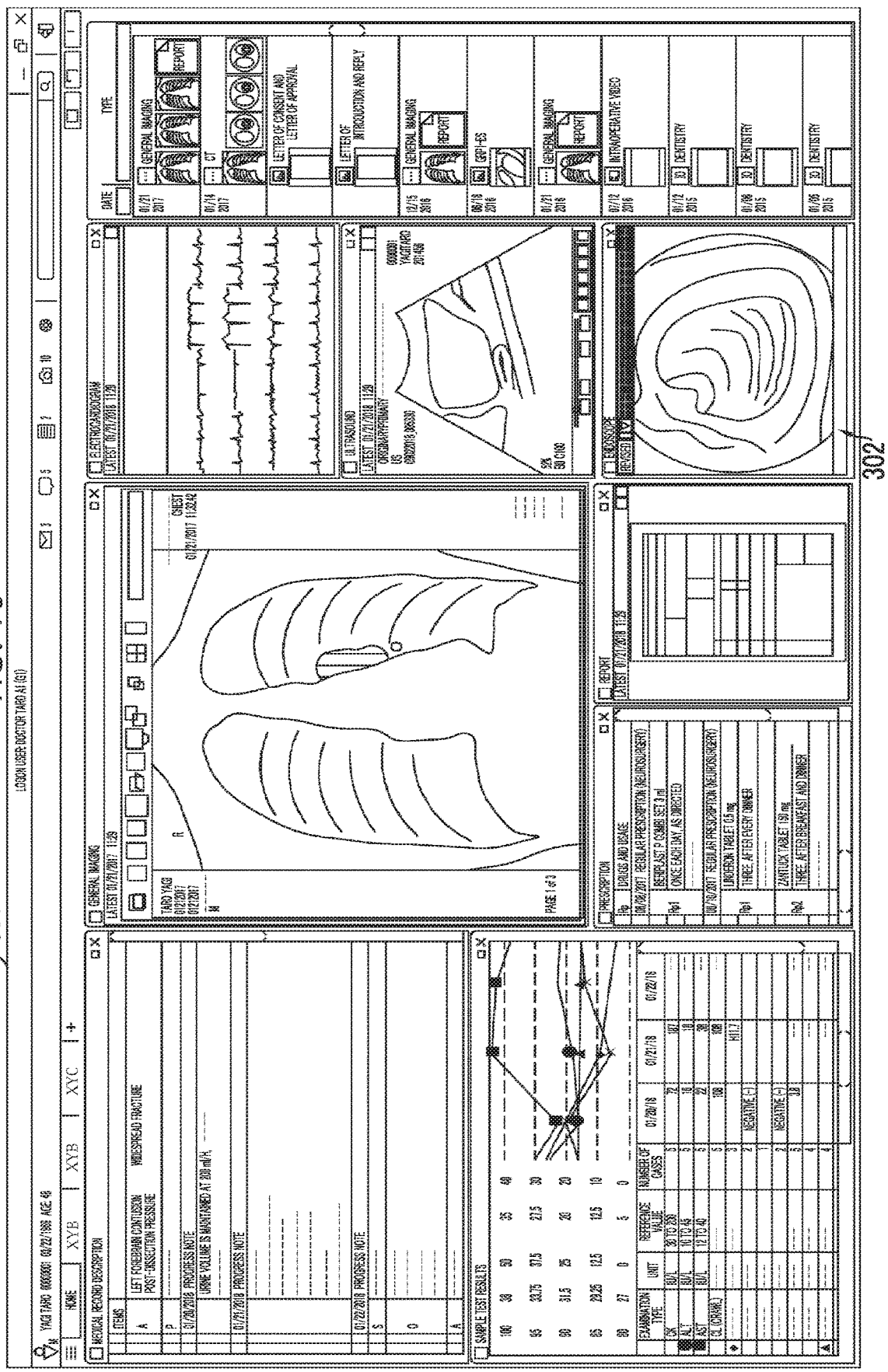
FIG. 16 is a diagram showing a layout screen.
Figures 17, 18:
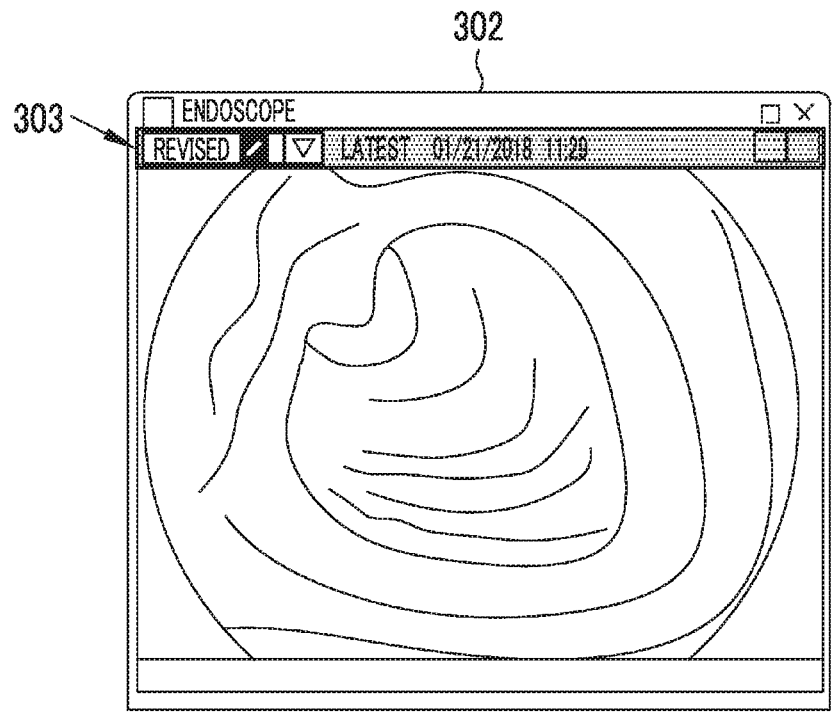
FIG. 17 is an enlarged view of an endoscope image field on the layout screen.
FIG. 18 is a diagram showing an unread data list screen.

As shown in FIG. 16, in a case where the display screen generation unit 62 generates or edits the layout screen 301, the unread management unit 63 can display the status of the medical examination process, such as unread, on the layout screen 301 similarly to the clinical flow screen 81 in the first embodiment. In FIG. 16, the unread management unit 63 displays the status of "revised" in the examination image of the endoscope in an endoscope image field 302 that configures a part of the layout screen 301. More specifically, as shown in FIG. 17, a status display field 303 for displaying revised and other statuses, such as unread, is provided in the endoscope image field 302. In the status display field 303, revised and other statuses, such as unread, are displayed by characters such as "revised", a badge indicating "revised" and the like, and/or coloring of the status display field 303. The form of the badge, the color for coloring, and the like are the same as in the first embodiment.

As described above, in the case of displaying a status such as unread on the layout screen 301, it is possible to grasp the status such as unread while viewing the outline of the medical examination process of the patient. In particular, in the case of displaying the status of "revised" on the layout screen 301, the process or result of other medical examination processes can be easily compared with the content of the medical examination process that has been "revised". Therefore, it is possible to advance an operation, such as diagnosis, especially quickly while grasping the content of "revised" exactly.

Fourth Embodiment

As shown in FIG. 18, in a case where the display screen generation unit 62 generates or edits the unread data list screen 401, the unread management unit 63 can display the status of the medical examination process, such as unread, on the unread data list screen 401 similarly to the clinical flow screen 81 in the first embodiment. In FIG. 18, a status field 402 for displaying a status, such as unread, is provided, and the characters of "unread" or "revised" are displayed in the status field 402, thereby displaying the status of "unread" or "revised" for the corresponding data. In addition, requesters are distinguished by giving the same color as the legend (refer to FIG. 11) in the first embodiment for each line, for example. In FIG. 18, the data type is an item of the medical examination process.

By generating and displaying the unread data list screen 401 as described above, it is possible to manage unread and the like in the entire facility, such as a hospital having the medical examination support system 10, and to reduce the oversight of the medical examination process that is unread or the like. This is because the unread or revised medical examination process can be viewed. In the case of the unread data list screen 401 on which unread and revised are displayed so as to be distinguished, consideration, such as giving priority to the medical examination process in a particularly important "revised" state, can be given. Therefore, a serious oversight can be reduced more reliably compared with a case of listing unread and revised so as not to be distinguished.

The display screen generation unit 62 and the unread management unit 63 can generate and edit an unread list display screen on which only the medical examination process in a new "unread" state is listed. Similarly, the display screen generation unit 62 and the unread management unit 63 can list only the medical examination process in a "revised" state. The same applies to the other statuses.

In the first embodiment and the like described above, a display screen, such as the clinical flow screen 81, is generated and displayed through the initial screen 71. However, a display screen, such as the clinical flow screen 81, can be generated indirectly from other apparatuses or systems that cooperate with the medical examination support apparatus 12. For example, since the electronic medical record server 21 can be operated directly from the client terminal 11, the clinical flow screen 81 can be called in the process of operating the electronic medical record server 21.

On a display screen, such as the clinical flow screen 81, the timeline screen 201, the layout screen 301, or the unread data list screen 401 in the first embodiment and the like, it is possible to optionally search, sort, or select patients, medical examination processes, or items included in the medical examination processes.

Conditions for Changing Status to Read

In principle, a status, such as unread, in the first embodiment and the like can be changed by any medical staff member who can log in to the medical examination support system 10. That is, the unread management unit 63 changes the status to read in a case where either a requester of the medical examination process whose status is unread or revised or a person other than the requester views the medical examination process whose status is unread or revised. For example, in a case where a medical examination process in the state of "unread" or "revised" is viewed by the requester of the medical examination process, the unread management unit 63 changes the status of the medical examination process to "read". Also in a case where a medical examination process in the state of "unread" or "revised" is viewed by a person other than the requester of the medical examination process, the unread management unit 63 changes the status of the medical examination process to "read". The reason why all medical staff members can change the unread or revised medical examination process to read as described above is that it is possible to reduce the oversight of the unread or revised medical examination process in terms of the entire medical facility such as a hospital.

However, in a case where the medical examination process whose status is unread or revised is viewed by a specific person (person who should read the medical examination process), the unread management unit 63 can change the status to read. For example, a person who can change the unread or revised medical examination process to the status of read may be limited only to a case where the requester himself or herself of the medical examination process views the unread or revised medical examination process. Alternatively, a person who can change the unread or revised medical examination process to the status of read may be limited to the requester himself or herself of the medical examination process ("oneself") or a person belonging to the group to which the requester of the medical examination process belongs ("oneselfs department"). As described above, in a case where a person who can change the status to read is limited to a specific person, the status is not set to read unless a person who should view an unread or revised medical examination process views the unread or revised medical examination process. Therefore, the person who should view the unread or revised medical examination process can reliably view the medical examination process. In addition, it is possible to prevent a mistake, such as a case where the status of the unread or revised medical examination process is changed to read since a person other than a person who should view the unread or revised medical examination process views the medical examination process, and accordingly, the person who should view the unread or revised medical examination process overlooks the unread or revised medical examination process.

In addition, the unread management unit 63 may change the status of the unread or revised medical examination process to read in a case where a plurality of medical staff members view the unread or revised medical examination process. In particular, the unread management unit 63 may change the status of the unread or revised medical examination process to read in a case where a plurality of specific medical staff members view the unread or revised medical examination process. This is useful in a case where a plurality of specific medical staff members should view the unread or revised medical examination process. For example, this is useful in a case where it is necessary to ask an attending doctor for viewing (approval) or the like in addition to a temporary responsible doctor (for example, a doctor in training).

In the first embodiment and the like described above, in a case where the medical staff member views a medical examination process whose status is unread or revised, the unread management unit 63 automatically changes the status of the viewed medical examination process to read even in a case where an explicit operation for changing the status to read is not performed. This is because it is not necessary to perform an explicit operation for changing the status to read as long as it is possible to prevent an oversight and accordingly, the operation load is small and the convenience is high. However, the unread management unit 63 can change the status of the unread or revised medical examination process to read in a case where an operation input to change the status of the unread or revised medical examination process to read is received. By making the status be changed to read first by an explicit operation, the status is not changed to read even in a case where a person who does not need to view the unread or revised medical examination process accidentally views the unread or revised medical examination process. Therefore, a person who should view the unread or revised medical examination process can reliably view the unread or revised medical examination process without overlooking the unread or revised medical examination process. The explicit operation for changing the status to read is a selection of a menu on the client terminal 11, click of a button or the like, or other operations.

The unread management unit 63 can receive an operation of changing (returning) the status of the read medical examination process to unread or revised. The operation of returning the status of read to unread or revised is a selection of a menu on the client terminal 11, click of a button or the like, or other operations. As described above, by allowing the status that has been changed to read once to be changed to unread or revised, the status is returned to the previous status even in a case where a person who does not need to view the unread or revised medical examination process accidentally changes the status to read. Therefore, a person who should view the unread or revised medical examination process can reliably view the unread or revised medical examination process without overlooking the unread or revised medical examination process.

Figure 19:
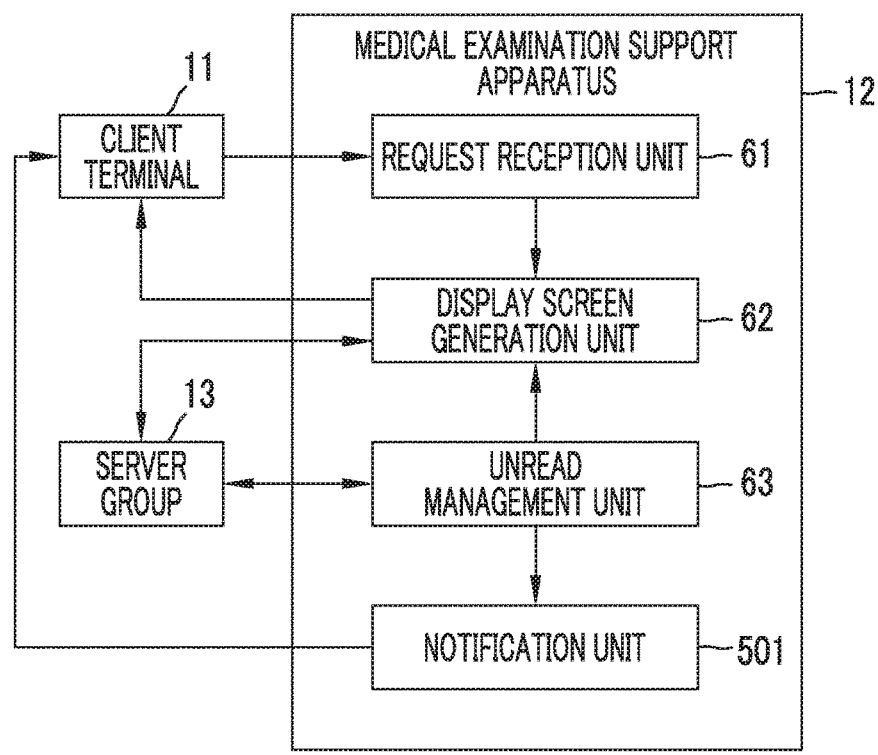
FIG. 19 is a diagram showing a medical examination support apparatus having a notification unit.

As shown in FIG. 19, it is preferable that the medical examination support apparatus 12 of the first embodiment and the like described above comprises the notification unit 501 that provides notification of the change of the status to unread or revised in a case where the client terminal 11 does not display the display screen generated by the display screen generation unit 62 on the display unit 36. The change of the status to unread means that a medical examination process whose status is not assigned due to acquisition of an examination image or a report or the like is registered with the status of unread. The notification unit 501 acquires, from the unread management unit 63, information indicating that the status of the medical examination process has been changed to unread or revised. The notification unit 501 is one function of the operating program 59, and the CPU 51 and the memory 52 cooperate with each other to function as the notification unit 501.

Figure 20:
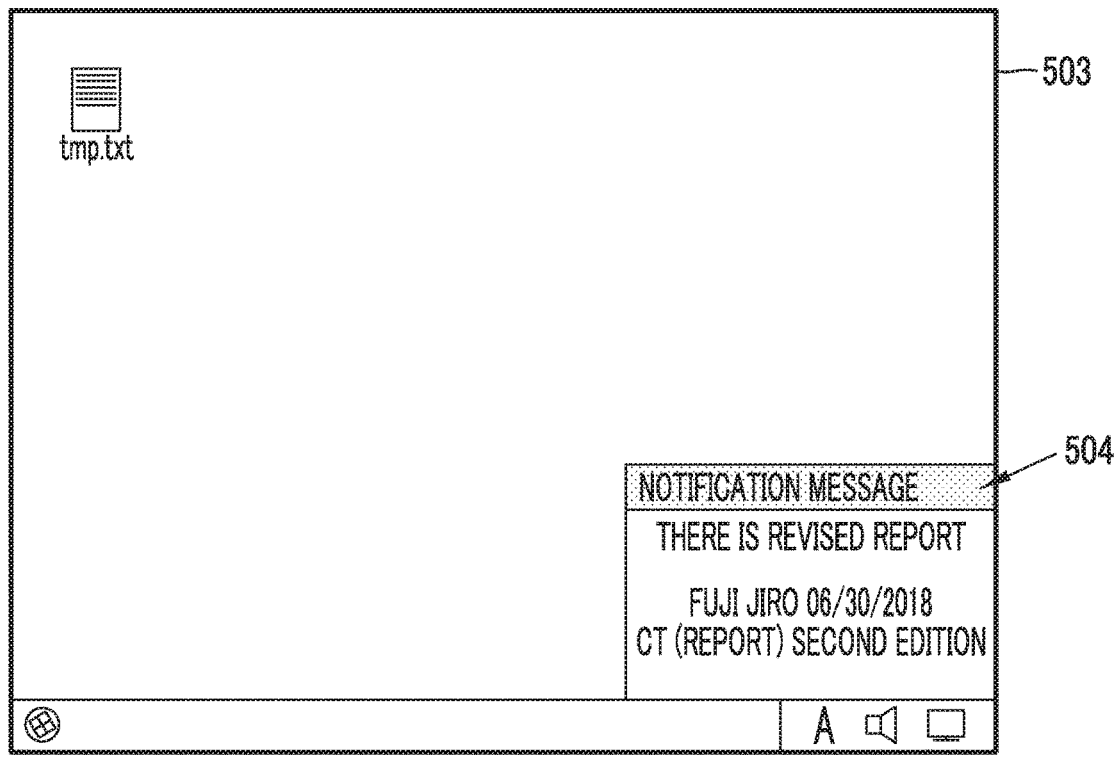
FIG. 20 is a schematic diagram showing a notification mode.

For example, as shown in FIG. 20, it is assumed that a display screen, such as the clinical flow screen 81, is minimized and the client terminal 11 displays a so-called desktop screen 503 on the display unit 36. In this case, in a case where the notification unit 501 acquires information indicating that the status of a specific medical examination process has been changed to unread or revised, the notification unit 501 displays a pop-up message 504 or the like on the desktop screen 503 (screen displayed by the client terminal 11) to notify the user of the client terminal 11 that the status of the specific medical examination process has been changed to unread or revised. The specific medical examination process is, for example, a medical examination process whose requester is the user of the client terminal 11 or a medical examination process whose requester is a medical staff member in the department of the user of the client terminal 11.

As described above, by providing notification in a case where the status of a specific medical examination process is changed to unread or revised, the existence of the specific medical examination process whose status has been newly changed to unread or revised can be known even in a case where a display screen provided by the medical examination support apparatus 12, such as the clinical flow screen 81, is not displayed. As a result, it is possible to reduce the oversight of the medical examination process.

The notification unit 501 can change the content of the notification in the pop-up message 504 or the like according to the setting. For example, a part of the notification content can be omitted or can be made as a secret letter. In the case of providing notification using the pop-up message 504, the notification unit 501 is useful in a case where a portion relevant to the personal information of a patient is omitted and a case where another patient is examined at a place where the client terminal 11 is located.

As shown in FIG. 21, it is preferable that the medical examination support apparatus 12 of the first embodiment and the like described above comprises a medical record writing unit 601 that automatically writes the content of a medical examination process whose status has been changed to read in an electronic medical record in a case where the status of the medical examination process is changed to read. The medical record writing unit 601 acquires, from the unread management unit 63, information indicating that the status of the medical examination process has been changed to read. The medical record writing unit 601 is one function of the operating program 59, and the CPU 51 and the memory 52 cooperate with each other to function as the medical record writing unit 601. In a case where the content of the medical examination process whose status has been changed to read is automatically written in the electronic medical record as described above, creation of an electronic medical record becomes easy. In addition, in a case where the medical record writing unit 601 automatically writes the content of the medical examination process whose status has been changed to read in the electronic medical record, the medical record writing unit 601 can receive an input of a comment of a medical staff member. In this case, creation of an electronic medical record becomes easier.

The medical examination support system 10 of the first embodiment and the like described above comprises the display screen generation unit 62 that generates a display screen for displaying a medical examination process and identification information of a patient so as to be associated with each other for each of a plurality of patients and the unread management unit 63 that displays a status, which includes information indicating that the medical examination process has been unread, or information indicating that the medical examination process has been read, or both the pieces of information, on the display screen. In a case where there is a revision in the medical examination process whose status is unread or read, the unread management unit 63 displays the status of the medical examination process, which has been revised, in a display mode different from display modes indicating unread and read.

In addition, the operating program 59 of the medical examination support apparatus 12 of the first embodiment and the like described above is a program that causes the CPU 51 or the CPU 51 and the memory 52 to function as the display screen generation unit 62 that generates a display screen for displaying a medical examination process and identification information of a patient so as to be associated with each other for each of a plurality of patients and the unread management unit 63 that displays a status, which includes information indicating that the medical examination process has been unread, or information indicating that the medical examination process has been read, or both the pieces of information, on the display screen and that, in a case where there is a revision in the medical examination process whose status is unread or read, causes the unread management unit 63 to display the status of the medical examination process, which has been revised, in a display mode different from display modes indicating unread and read.

An operation method of the medical examination support apparatus 12 of the first embodiment and the like described above is an operation method of the medical examination support apparatus 12 comprising the display screen generation unit 62 that generates a display screen for displaying a medical examination process and identification information of a patient so as to be associated with each other for each of a plurality of patients and the unread management unit 63 that displays a status, which includes information indicating that the medical examination process has been unread, or information indicating that the medical examination process has been read, or both the pieces of information, on the display screen. The operation method of the medical examination support apparatus 12 comprises a step in which, in a case where there is a revision in the medical examination process whose status is unread or read, the unread management unit 63 displays the status of the medical examination process, which has been revised, in a display mode different from display modes indicating unread and read.

An operation method of the medical examination support system 10 of the first embodiment and the like described above is an operation method of the medical examination support system 10 comprising the display screen generation unit 62 that generates a display screen for displaying a medical examination process and identification information of a patient so as to be associated with each other for each of a plurality of patients and the unread management unit 63 that displays a status, which includes information indicating that the medical examination process has been unread, or information indicating that the medical examination process has been read, or both the pieces of information, on the display screen. The operation method of the medical examination support system 10 comprises a step in which, in a case where there is a revision in the medical examination process whose status is unread or read, the unread management unit 63 displays the status of the medical examination process, which has been revised, in a display mode different from display modes indicating unread and read.

In the first embodiment and the like described above, the hardware structures of processing units for executing various kinds of processing, such as the GUI controller 41, the request issuing unit 42, the request reception unit 61, the display screen generation unit 62, the unread management unit 63, the notification unit 501, and the medical record writing unit 601, are various processors shown below. The various processors include a central processing unit (CPU) that is a general-purpose processor that executes software (program) to function as various processing units, a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute various kinds of processing.

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: medical examination support system
11: client terminal
12: medical examination support apparatus
13: server group
14: network
21: electronic medical record server
21A: medical record database
22: image server
22A: image database
23: report server
23A: report database
32: memory
33: storage
34: communication unit
35: connection circuit
36: display unit
37: operation unit
39: operating program
41: GUI controller
42: request issuing unit
52: memory
53: storage
54: communication unit
55: connection circuit
59: operating program
61: request reception unit
62: display screen generation unit
63: unread management unit
66: display controller
71: initial screen
72: schedule display field
73: e-mail display field
74: list display field
78: scroll bar
79: scroll bar
81: clinical flow screen
82: clinical flow display field
201: timeline screen
301: layout screen
302: endoscope image field
303: status display field
401: unread data list screen
402: status field
501: notification unit
503: desktop screen 504: pop-up message
601: medical record writing unit
A1: doctor
A2: doctor
B1: doctor
C01: patient column
C02: unread number management column
C03: biopsy column
C04: radiation column
C05: endoscope column
C06: pathological column
C07: echocardiographic column
G1: group
G19: group
G2: group
L01: item display row
N1: technician
S1: first row
S2: second row
S3: third row

What is claimed is:

1. A medical examination support apparatus, comprising:
a display screen generation unit that generates a display screen for displaying a medical examination process and identification information of a patient so as to be associated with each other for each of a plurality of patients;
an unread management unit that displays a status, which includes information indicating that the medical examination process has been unread, or information indicating that the medical examination process has been read, or both the pieces of information, on the display screen; and
a medical record writing unit that only writes a content of the medical examination process whose status has been changed to read in an electronic medical record in a case where the status is changed to read,
wherein, in a case where there is a revision in the medical examination process whose status is unread or read, the unread management unit displays the status of the medical examination process, which has been revised, in a display mode different from display modes indicating unread and read, and
wherein the unread management unit changes the status to read only in a case where the medical examination process whose status is unread or revised is viewed by all of a plurality of specific persons predetermined from those who can view the medical examination process.

2. The medical examination support apparatus according to claim 1,
wherein the unread management unit displays the status of the medical examination process, which is requested by a person who views the display screen, and the status of the medical examination process, which is requested by a person other than the person who views the display screen, in different display modes.

3. The medical examination support apparatus according to claim 1,
wherein the unread management unit displays the status of the medical examination process, which is requested by a person belonging to a group to which a person who views the display screen belongs, and the status of the medical examination process, which is requested by a person belonging to a group to which the person who views the display screen does not belong, in different display modes.

4. The medical examination support apparatus according to claim 1,
wherein the unread management unit displays the status of the medical examination process requested by a person who views the display screen, the status of the medical examination process requested by a person who is other than the person who views the display screen and who belongs to a group to which the person who views the display screen belongs, and the status of the medical examination process requested by a person belonging to a group to which the person who views the display screen does not belong, in different display modes.

5. The medical examination support apparatus according to claim 1,
wherein the unread management unit displays the status of the specific medical examination process having a setting indicating important and the status of the medical examination process not having the setting in different display modes.

6. The medical examination support apparatus according to claim 1,
wherein the unread management unit displays the status according to presence or absence of a specific mark attached to the medical examination process.

7. The medical examination support apparatus according to claim 1,
wherein the display screen comprises an unread number display field for displaying the number of medical examination processes whose status is unread or revised for each patient.

8. The medical examination support apparatus according to claim 1,
wherein the unread management unit acquires a part or entirety of the status from other apparatuses or systems that cooperate with the medical examination support apparatus.

9. The medical examination support apparatus according to claim 1,
wherein the unread management unit changes the status to read in a case where either a requester of the medical examination process whose status is unread or revised or a person other than the requester views the medical examination process whose status is unread or revised.

10. The medical examination support apparatus according to claim 1,
wherein the unread management unit changes the status to read in a case where the medical examination process whose status is unread or revised is viewed by a specific person.

11. The medical examination support apparatus according to claim 1,
wherein the unread management unit changes the status to read in a case where an operation input to change the status of the medical examination process whose status is unread or revised to read is received.

12. The medical examination support apparatus according to claim 1,
wherein, in a case where the display screen generation unit generates or edits a timeline display screen for displaying the medical examination process in time series for one specific patient, the unread management unit displays the status of the medical examination process on the timeline display screen.

13. The medical examination support apparatus according to claim 1, wherein, in a case where the display screen generation unit generates or edits a layout screen for displaying the medical examination process side by side on one screen for one specific patient, the unread management unit displays the status of the medical examination process on the layout screen.

14. The medical examination support apparatus according to claim 1, further comprising:
a notification unit that provides notification of a change of the status to unread or revised in a case where the display screen is not displayed on a display unit.

15. The medical examination support apparatus according to claim 1, wherein a plurality of examination items are listed on the display screen.

16. The medical examination support apparatus according to claim 1, wherein at least one of a plurality of examination items includes an image and a report as medical examination data, and each of the image and the report is displayed distinguishably according to one of first to third display modes according to the status.

17. The medical examination support apparatus according to claim 1, wherein
the unread management unit displays the status of a specific medical examination process having a setting indicating important and the status of a medical examination process not having the setting in different display modes, and
for each item of the medical examination process, display modes having different shapes or patterns indicating that the status is unread, revised, and important are displayed alternatively or coexistingly.

18. The medical examination support apparatus according to claim 1, wherein the medical record writing unit receives an input of a comment as a content of the medical examination process.

19. The medical examination support apparatus according to claim 1, wherein
at least one of a plurality of examination items includes an image and a report as medical examination data,
the image and the report are respectively represented by an image icon and a report icon,
each of the image icon and the report icon is displayed with one of status icons added according to the status of each of the image and the report, and
each of the status icons is different respectively.

20. The medical examination support apparatus according to claim 1, wherein
the unread management unit displays the status of a specific medical examination process having a setting indicating important and the status of a medical examination process not having the setting in different display modes, and
in case the status of each item of the medical examination process is unread or revised, a display mode indicating unread or revised and important is different from a display mode indicating unread or revised and not important.

* * * * *